(12) United States Patent
Lopez-Berestein et al.

(10) Patent No.: US 12,077,760 B2
(45) Date of Patent: Sep. 3, 2024

(54) DNA APTAMERS AND USE THEREOF FOR THE TREATMENT OF CANCER

(71) Applicants: Board of Regents, The University of Texas System, Austin, TX (US); Consiglio Nazionale delle Ricerche, Rome (IT)

(72) Inventors: Gabriel Lopez-Berestein, Houston, TX (US); Paola Amero, Houston, TX (US); Cristian Rodriguez-Aguayo, Houston, TX (US); Rahul Mitra, Houston, TX (US); Anil K. Sood, Houston, TX (US); Vittorio De Franciscis, Naples (IT); David Volk, Houston, TX (US); Lokesh Ganesh L. Rao, Houston, TX (US)

(73) Assignees: Board of Regents, The University of Texas System, Austin, TX (US); Consiglio Nazionale delle Ricerche, Rome (IT)

( * ) Notice: Subject to any disclaimer, the term of this patent is extended or adjusted under 35 U.S.C. 154(b) by 182 days.

(21) Appl. No.: 17/413,550

(22) PCT Filed: Dec. 16, 2019

(86) PCT No.: PCT/US2019/066654
§ 371 (c)(1),
(2) Date: Jun. 12, 2021

(87) PCT Pub. No.: WO2020/124095
PCT Pub. Date: Jun. 18, 2020

(65) Prior Publication Data
US 2022/0380766 A1    Dec. 1, 2022

Related U.S. Application Data

(60) Provisional application No. 62/780,058, filed on Dec. 14, 2018.

(51) Int. Cl.
| | |
|---|---|
| *C12N 15/115* | (2010.01) |
| *A61K 31/337* | (2006.01) |
| *A61K 33/243* | (2019.01) |
| *A61P 35/00* | (2006.01) |

(52) U.S. Cl.
CPC .......... *C12N 15/115* (2013.01); *A61K 31/337* (2013.01); *A61K 33/243* (2019.01); *A61P 35/00* (2018.01); *C12N 2310/16* (2013.01); *C12N 2310/313* (2013.01); *C12N 2310/322* (2013.01); *C12N 2310/351* (2013.01); *C12N 2310/531* (2013.01); *C12N 2320/31* (2013.01); *C12N 2320/32* (2013.01)

(58) Field of Classification Search
CPC .............. C12N 15/115; C12N 2310/16; C12N 2310/313; C12N 2310/322; C12N 2310/351; C12N 2310/531; C12N 2310/346; A61P 35/00
See application file for complete search history.

(56) References Cited

U.S. PATENT DOCUMENTS

| | | | |
|---|---|---|---|
| 8,741,870 B2 | 6/2014 | De Franciscis et al. | |
| 2004/0242521 A1 | 12/2004 | Gorenstein et al. | |
| 2009/0170219 A1* | 7/2009 | Nakamura ........... | C07K 16/065 530/390.5 |
| 2010/0004432 A1* | 1/2010 | Miyakawa ........... | C12N 15/115 536/23.5 |
| 2013/0197070 A1 | 8/2013 | De Franciscis et al. | |

OTHER PUBLICATIONS

Walsh et al., (Biochemical and Biophysical Research Communications 388 (2009) 732-735) (Year: 2009).*
Alvarez-Martos et al., (Biochemical and Biophysical Research Communications 489 (2017) 381-385) (Year: 2017).*
Hwang et al (Transl Cancer Res 2021; 10(2):1025-1033) (Year: 2021).*
Glen Report 17(1): 7, 2004) (Year: 2004).*
Ni et al., (Int. J. Mol. Sci. 2017, 18:1683, 21 pages) (Year: 2017).*
Amero, P. et al. "Conversion of RNA Aptamer into Modified DNA Aptamers Provides for Prolonged Stability and Enhanced Antitumor Activity," *Journal of the American Chemical Society*, 143 (2021): 7655-7670.
Amero, P. et al. "Development of novel modified aptamers to target Axl receptor in ovarian cancer," *Annals of Oncology*, 29.3 (2018): iii17.
Cerchia, L. et al., Targeting Axl With an High-affinity Inhibitory Aptamer. *Molecular Therapy*, 20. 12 (2012):2291-2303.
Extended European Search Report issued in European Patent Application No. 19896984.2, dated Sep. 8, 2022.
Haruta, K. et al., "A Novel PEGylation Method for Improving the Pharmacokinetic Properties of Anti-Interleukin-17A RNA Aptamers," *Nucleic and Therapeutics*, 27.1 (2017): 36-44.

(Continued)

*Primary Examiner* — Richard A Schnizer
(74) *Attorney, Agent, or Firm* — Parker Highlander PLLC

(57) ABSTRACT

Provided herein are DNA aptamers targeting AXL receptor kinase. The DNA aptamers may comprise a thiophosphate backbone and be chemically modified. Further provided herein are methods of use thereof for the treatment of a disease or disorder, such as cancer.

14 Claims, 14 Drawing Sheets

Specification includes a Sequence Listing.

(56) References Cited

OTHER PUBLICATIONS

Kanlikilicer, P. et al. "Therapeutic Targeting of AXL Receptor Tyrosine Kinase Inhibits Tumor Growth and Intraperitoneal Metastasis in Ovarian Cancer Models," *Molecular Therapy Nucleic Acids*, 9 (2017):251-262.

Morita, Y. et al., "Aptamer Therapeutics in Cancer: Current and Future," *Cancers*, 10 (2018): 1-22.

PCT International Preliminary Report on Patentability issued in International Patent Application No. PCT/US2019/066654, dated Jun. 24, 2021.

PCT International Search Report and Written Opinion issued in International Patent Application No. PCT/US2019/066654, dated Mar. 23, 2020.

Volk, D. et al. "Development of Phosphorothioate DNA and DNA Thioaptamers," *biomedicines*, 5.41 (2017): 1-20.

\* cited by examiner

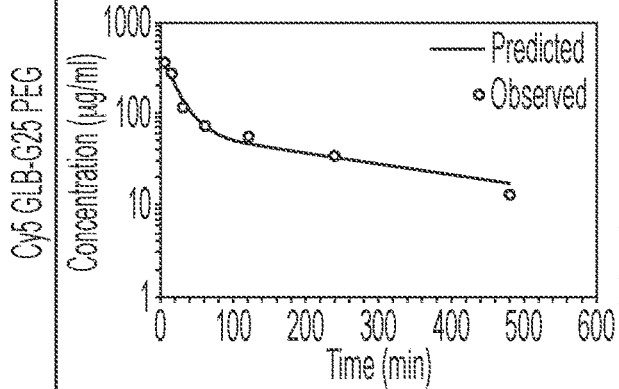
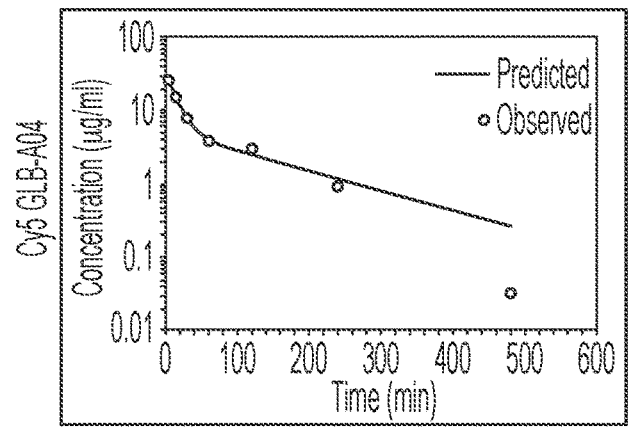
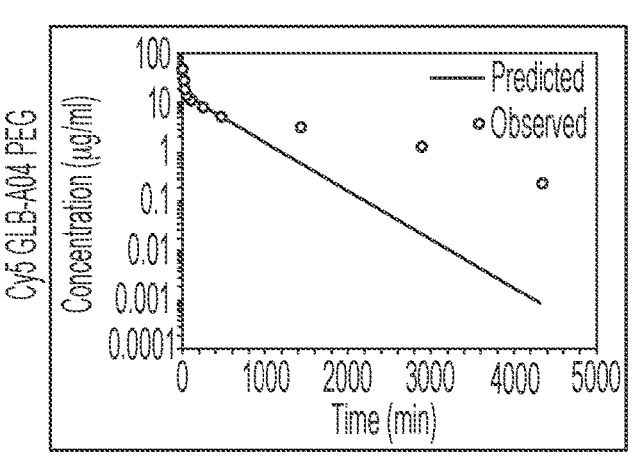
FIGS. 3B-3C

A

C, T 2' Fluoro dC, 2' Fluoro dU
a,c,g,t 3' monoth o dN
6 – 3' dth o dA
8 – 3' dth o dG

| | | |
|---|---|---|
| (SEQ ID NO: 1) | GLB B0 (DNA) | aTgATCAATcGCCCTCAaTTCGACAgGAGGCtCaC |
| (SEQ ID NO: 2) | GLB PS2 G03 | aT8ATCAATcGCCCTCAaTTCGACAgGAGGCtCaC |
| (SEQ ID NO: 3) | GLB PS2 G11 | aTgATCAATc8CCCTCAaTTCGACAgGAGGCtCaC |
| (SEQ ID NO: 4) | GLB PS2 G21 | aTgATCAATcGCCCTCAaTTC8ACAgGAGGCtCaC |
| (SEQ ID NO: 5) | GLB PS2 G25 | aTgATCAATcGCCCTCAaTTCGACA8GAGGCtCaC |
| (SEQ ID NO: 6) | GLB PS2 G26 | aTgATCAATcGCCCTCAaTTCGACAg8AGGCtCaC |
| (SEQ ID NO: 7) | GLB PS2 G28 | aTgATCAATcGCCCTCAaTTCGACAgGA8GCtCaC |
| (SEQ ID NO: 8) | GLB PS2 G29 | aTgATCAATcGCCCTCAaTTCGACAgGAG8CtCaC |
| (SEQ ID NO: 9) | GLB PS2 A01 | 6TgATCAATcGCCCTCAaTTCGACAgGAGGCtCaC |
| (SEQ ID NO: 10) | GLB PS2 A04 | aTg6TCAATcGCCCTCAaTTCGACAgGAGGCtCaC |
| (SEQ ID NO: 11) | GLB PS2 A07 | aTgATC6ATcGCCCTCAaTTCGACAgGAGGCtCaC |
| (SEQ ID NO: 12) | GLB PS2 A08 | aTgATCA6TcGCCCTCAaTTCGACAgGAGGCtCaC |
| (SEQ ID NO: 13) | GLB-PS2-A16 | aTgATCAATcGCCCTC6aTTCGACAgGAGGCtCaC |
| (SEQ ID NO: 14) | GLB PS2 A17 | aTgATCAATcGCCCTCA6TTCGACAgGAGGCtCaC |
| (SEQ ID NO: 15) | GLB PS2 A22 | aTgATCAATcGCCCTCAaTTCG6CAgGAGGCtCaC |
| (SEQ ID NO: 16) | GLB-PS2-A2 | aTgATCAATcGCCCTCAaTTCGAC6gGAGGCtCaC |
| (SEQ ID NO: 17) | GLB PS2 A27 | aTgATCAATcGCCCTCAaTTCGACAgg6GGCtCaC |
| (SEQ ID NO: 18) | GLB PS2 A33 | aTgATCAATcGCCCTCAaTTCGACAgGAGGCtC6C |

FIG. 6A

SEQUENCE LISTING

```
<160> NUMBER OF SEQ ID NOS: 20

<210> SEQ ID NO 1
<211> LENGTH: 34
<212> TYPE: DNA
<213> ORGANISM: Artificial Sequence
<220> FEATURE:
<223> OTHER INFORMATION: Synthetic aptamer
<220> FEATURE:
<221> NAME/KEY: misc_feature
<222> LOCATION: (2)..(2)
<223> OTHER INFORMATION: n is 2'fluorouridine
<220> FEATURE:
<221> NAME/KEY: misc_feature
<222> LOCATION: (5)..(5)
<223> OTHER INFORMATION: n is 2'fluorouridine
<220> FEATURE:
<221> NAME/KEY: modified_base
<222> LOCATION: (6)..(6)
<223> OTHER INFORMATION: 2'fluorocytidine
<220> FEATURE:
<221> NAME/KEY: misc_feature
<222> LOCATION: (9)..(9)
<223> OTHER INFORMATION: n is 2'fluorouridine
<220> FEATURE:
<221> NAME/KEY: modified_base
<222> LOCATION: (12)..(13)
<223> OTHER INFORMATION: 2'fluorocytidine
<220> FEATURE:
<221> NAME/KEY: misc_feature
<222> LOCATION: (14)..(14)
<223> OTHER INFORMATION: n is 2'fluorouridine
<220> FEATURE:
<221> NAME/KEY: modified_base
<222> LOCATION: (15)..(15)
<223> OTHER INFORMATION: 2'fluorocytidine
<220> FEATURE:
<221> NAME/KEY: misc_feature
<222> LOCATION: (18)..(19)
<223> OTHER INFORMATION: n is 2'fluorouridine
<220> FEATURE:
<221> NAME/KEY: modified_base
<222> LOCATION: (20)..(20)
<223> OTHER INFORMATION: 2'fluorocytidine
<220> FEATURE:
<221> NAME/KEY: modified_base
<222> LOCATION: (23)..(23)
<223> OTHER INFORMATION: 2'fluorocytidine
<220> FEATURE:
<221> NAME/KEY: modified_base
<222> LOCATION: (32)..(32)
<223> OTHER INFORMATION: 2'fluorocytidine
<220> FEATURE:
<221> NAME/KEY: modified_base
<222> LOCATION: (34)..(34)
<223> OTHER INFORMATION: 2'fluorocytidine
```

```
<400> SEQUENCE: 1
angancaanc gccncaannc gacaggaggc tcac                                34

<210> SEQ ID NO 2
<211> LENGTH: 34
<212> TYPE: DNA
<213> ORGANISM: Artificial Sequence
<220> FEATURE:
<223> OTHER INFORMATION: Synthetic aptamer
<220> FEATURE:
<221> NAME/KEY: misc_feature
<222> LOCATION: (2)..(2)
<223> OTHER INFORMATION: n is 2'fluorouridine
<220> FEATURE:
<221> NAME/KEY: modified_base
<222> LOCATION: (3)..(3)
<223> OTHER INFORMATION: g = dithiophosphate guanine
<220> FEATURE:
<221> NAME/KEY: misc_feature
<222> LOCATION: (5)..(5)
<223> OTHER INFORMATION: n is 2'fluorouridine
<220> FEATURE:
<221> NAME/KEY: modified_base
<222> LOCATION: (6)..(6)
<223> OTHER INFORMATION: 2'fluorocytidine
<220> FEATURE:
<221> NAME/KEY: misc_feature
<222> LOCATION: (9)..(9)
<223> OTHER INFORMATION: n is 2'fluorouridine
<220> FEATURE:
<221> NAME/KEY: modified_base
<222> LOCATION: (12)..(13)
<223> OTHER INFORMATION: 2'fluorocytidine
<220> FEATURE:
<221> NAME/KEY: misc_feature
<222> LOCATION: (14)..(14)
<223> OTHER INFORMATION: n is 2'fluorouridine
<220> FEATURE:
<221> NAME/KEY: modified_base
<222> LOCATION: (15)..(15)
<223> OTHER INFORMATION: 2'fluorocytidine
<220> FEATURE:
<221> NAME/KEY: misc_feature
<222> LOCATION: (18)..(19)
<223> OTHER INFORMATION: n is 2'fluorouridine
<220> FEATURE:
<221> NAME/KEY: modified_base
<222> LOCATION: (20)..(20)
<223> OTHER INFORMATION: 2'fluorocytidine
<220> FEATURE:
<221> NAME/KEY: modified_base
<222> LOCATION: (23)..(23)
<223> OTHER INFORMATION: 2'fluorocytidine
<220> FEATURE:
<221> NAME/KEY: modified_base
<222> LOCATION: (32)..(32)
<223> OTHER INFORMATION: 2'fluorocytidine
<220> FEATURE:
<221> NAME/KEY: modified_base
<222> LOCATION: (34)..(34)
<223> OTHER INFORMATION: 2'fluorocytidine

<400> SEQUENCE: 2
angancaanc gccncaannc gacaggaggc tcac                                34

<210> SEQ ID NO 3
<211> LENGTH: 34
<212> TYPE: DNA
<213> ORGANISM: Artificial Sequence
<220> FEATURE:
<223> OTHER INFORMATION: Synthetic aptamer
<220> FEATURE:
<221> NAME/KEY: misc_feature
<222> LOCATION: (2)..(2)
<223> OTHER INFORMATION: n is 2'fluorouridine
```

```
<220> FEATURE:
<221> NAME/KEY: misc_feature
<222> LOCATION: (5)..(5)
<223> OTHER INFORMATION: n is 2'fluorouridine
<220> FEATURE:
<221> NAME/KEY: modified_base
<222> LOCATION: (6)..(6)
<223> OTHER INFORMATION: 2'fluorocytidine
<220> FEATURE:
<221> NAME/KEY: misc_feature
<222> LOCATION: (9)..(9)
<223> OTHER INFORMATION: n is 2'fluorouridine
<220> FEATURE:
<221> NAME/KEY: modified_base
<222> LOCATION: (11)..(11)
<223> OTHER INFORMATION: g = dithiophosphate guanine
<220> FEATURE:
<221> NAME/KEY: modified_base
<222> LOCATION: (12)..(13)
<223> OTHER INFORMATION: 2'fluorocytidine
<220> FEATURE:
<221> NAME/KEY: misc_feature
<222> LOCATION: (14)..(14)
<223> OTHER INFORMATION: n is 2'fluorouridine
<220> FEATURE:
<221> NAME/KEY: modified_base
<222> LOCATION: (15)..(15)
<223> OTHER INFORMATION: 2'fluorocytidine
<220> FEATURE:
<221> NAME/KEY: misc_feature
<222> LOCATION: (18)..(19)
<223> OTHER INFORMATION: n is 2'fluorouridine
<220> FEATURE:
<221> NAME/KEY: modified_base
<222> LOCATION: (20)..(20)
<223> OTHER INFORMATION: 2'fluorocytidine
<220> FEATURE:
<221> NAME/KEY: modified_base
<222> LOCATION: (23)..(23)
<223> OTHER INFORMATION: 2'fluorocytidine
<220> FEATURE:
<221> NAME/KEY: modified_base
<222> LOCATION: (32)..(32)
<223> OTHER INFORMATION: 2'fluorocytidine
<220> FEATURE:
<221> NAME/KEY: modified_base
<222> LOCATION: (34)..(34)
<223> OTHER INFORMATION: 2'fluorocytidine

<400> SEQUENCE: 3
angancaanc gccncaannc gacaggaggc tcac                                    34

<210> SEQ ID NO 4
<211> LENGTH: 34
<212> TYPE: DNA
<213> ORGANISM: Artificial Sequence
<220> FEATURE:
<223> OTHER INFORMATION: Synthetic aptamer
<220> FEATURE:
<221> NAME/KEY: misc_feature
<222> LOCATION: (2)..(2)
<223> OTHER INFORMATION: n is 2'fluorouridine
<220> FEATURE:
<221> NAME/KEY: misc_feature
<222> LOCATION: (5)..(5)
<223> OTHER INFORMATION: n is 2'fluorouridine
<220> FEATURE:
<221> NAME/KEY: modified_base
<222> LOCATION: (6)..(6)
<223> OTHER INFORMATION: 2'fluorocytidine
<220> FEATURE:
<221> NAME/KEY: misc_feature
<222> LOCATION: (9)..(9)
<223> OTHER INFORMATION: n is 2'fluorouridine
<220> FEATURE:
<221> NAME/KEY: modified_base
<222> LOCATION: (12)..(13)
```

```
<223> OTHER INFORMATION: 2'fluorocytidine
<220> FEATURE:
<221> NAME/KEY: misc_feature
<222> LOCATION: (14)..(14)
<223> OTHER INFORMATION: n is 2'fluorouridine
<220> FEATURE:
<221> NAME/KEY: modified_base
<222> LOCATION: (15)..(15)
<223> OTHER INFORMATION: 2'fluorocytidine
<220> FEATURE:
<221> NAME/KEY: misc_feature
<222> LOCATION: (18)..(19)
<223> OTHER INFORMATION: n is 2'fluorouridine
<220> FEATURE:
<221> NAME/KEY: modified_base
<222> LOCATION: (20)..(20)
<223> OTHER INFORMATION: 2'fluorocytidine
<220> FEATURE:
<221> NAME/KEY: modified_base
<222> LOCATION: (21)..(21)
<223> OTHER INFORMATION: g = dithiophosphate guanine
<220> FEATURE:
<221> NAME/KEY: modified_base
<222> LOCATION: (23)..(23)
<223> OTHER INFORMATION: 2'fluorocytidine
<220> FEATURE:
<221> NAME/KEY: modified_base
<222> LOCATION: (32)..(32)
<223> OTHER INFORMATION: 2'fluorocytidine
<220> FEATURE:
<221> NAME/KEY: modified_base
<222> LOCATION: (34)..(34)
<223> OTHER INFORMATION: 2'fluorocytidine

<400> SEQUENCE: 4
angancaanc gccncaannc gacaggaggc tcac                               34

<210> SEQ ID NO 5
<211> LENGTH: 34
<212> TYPE: DNA
<213> ORGANISM: Artificial Sequence
<220> FEATURE:
<223> OTHER INFORMATION: Synthetic aptamer
<220> FEATURE:
<221> NAME/KEY: misc_feature
<222> LOCATION: (2)..(2)
<223> OTHER INFORMATION: n is 2'fluorouridine
<220> FEATURE:
<221> NAME/KEY: misc_feature
<222> LOCATION: (5)..(5)
<223> OTHER INFORMATION: n is 2'fluorouridine
<220> FEATURE:
<221> NAME/KEY: modified_base
<222> LOCATION: (6)..(6)
<223> OTHER INFORMATION: 2'fluorocytidine
<220> FEATURE:
<221> NAME/KEY: misc_feature
<222> LOCATION: (9)..(9)
<223> OTHER INFORMATION: n is 2'fluorouridine
<220> FEATURE:
<221> NAME/KEY: modified_base
<222> LOCATION: (12)..(13)
<223> OTHER INFORMATION: 2'fluorocytidine
<220> FEATURE:
<221> NAME/KEY: misc_feature
<222> LOCATION: (14)..(14)
<223> OTHER INFORMATION: n is 2'fluorouridine
<220> FEATURE:
<221> NAME/KEY: modified_base
<222> LOCATION: (15)..(15)
<223> OTHER INFORMATION: 2'fluorocytidine
<220> FEATURE:
<221> NAME/KEY: misc_feature
<222> LOCATION: (18)..(19)
<223> OTHER INFORMATION: n is 2'fluorouridine
<220> FEATURE:
<221> NAME/KEY: modified_base
```

```
<222> LOCATION: (20)..(20)
<223> OTHER INFORMATION: 2'fluorocytidine
<220> FEATURE:
<221> NAME/KEY: modified_base
<222> LOCATION: (23)..(23)
<223> OTHER INFORMATION: 2'fluorocytidine
<220> FEATURE:
<221> NAME/KEY: modified_base
<222> LOCATION: (25)..(25)
<223> OTHER INFORMATION: g = dithiophosphate guanine
<220> FEATURE:
<221> NAME/KEY: modified_base
<222> LOCATION: (32)..(32)
<223> OTHER INFORMATION: 2'fluorocytidine
<220> FEATURE:
<221> NAME/KEY: modified_base
<222> LOCATION: (34)..(34)
<223> OTHER INFORMATION: 2'fluorocytidine

<400> SEQUENCE: 5
angancaanc gccncaannc gacaggaggc tcac                           34

<210> SEQ ID NO 6
<211> LENGTH: 34
<212> TYPE: DNA
<213> ORGANISM: Artificial Sequence
<220> FEATURE:
<223> OTHER INFORMATION: Synthetic aptamer
<220> FEATURE:
<221> NAME/KEY: misc_feature
<222> LOCATION: (2)..(2)
<223> OTHER INFORMATION: n is 2'fluorouridine
<220> FEATURE:
<221> NAME/KEY: misc_feature
<222> LOCATION: (5)..(5)
<223> OTHER INFORMATION: n is 2'fluorouridine
<220> FEATURE:
<221> NAME/KEY: modified_base
<222> LOCATION: (6)..(6)
<223> OTHER INFORMATION: 2'fluorocytidine
<220> FEATURE:
<221> NAME/KEY: misc_feature
<222> LOCATION: (9)..(9)
<223> OTHER INFORMATION: n is 2'fluorouridine
<220> FEATURE:
<221> NAME/KEY: modified_base
<222> LOCATION: (12)..(13)
<223> OTHER INFORMATION: 2'fluorocytidine
<220> FEATURE:
<221> NAME/KEY: misc_feature
<222> LOCATION: (14)..(14)
<223> OTHER INFORMATION: n is 2'fluorouridine
<220> FEATURE:
<221> NAME/KEY: modified_base
<222> LOCATION: (15)..(15)
<223> OTHER INFORMATION: 2'fluorocytidine
<220> FEATURE:
<221> NAME/KEY: misc_feature
<222> LOCATION: (18)..(19)
<223> OTHER INFORMATION: n is 2'fluorouridine
<220> FEATURE:
<221> NAME/KEY: modified_base
<222> LOCATION: (20)..(20)
<223> OTHER INFORMATION: 2'fluorocytidine
<220> FEATURE:
<221> NAME/KEY: modified_base
<222> LOCATION: (23)..(23)
<223> OTHER INFORMATION: 2'fluorocytidine
<220> FEATURE:
<221> NAME/KEY: modified_base
<222> LOCATION: (26)..(26)
<223> OTHER INFORMATION: g = dithiophosphate guanine
<220> FEATURE:
<221> NAME/KEY: modified_base
<222> LOCATION: (32)..(32)
<223> OTHER INFORMATION: 2'fluorocytidine
<220> FEATURE:
```

```
<221> NAME/KEY: modified_base
<222> LOCATION: (34)..(34)
<223> OTHER INFORMATION: 2'fluorocytidine

<400> SEQUENCE: 6
angancaanc gccncaannc gacaggaggc tcac                              34

<210> SEQ ID NO 7
<211> LENGTH: 34
<212> TYPE: DNA
<213> ORGANISM: Artificial Sequence
<220> FEATURE:
<223> OTHER INFORMATION: Synthetic aptamer
<220> FEATURE:
<221> NAME/KEY: misc_feature
<222> LOCATION: (2)..(2)
<223> OTHER INFORMATION: n is 2'fluorouridine
<220> FEATURE:
<221> NAME/KEY: misc_feature
<222> LOCATION: (5)..(5)
<223> OTHER INFORMATION: n is 2'fluorouridine
<220> FEATURE:
<221> NAME/KEY: modified_base
<222> LOCATION: (6)..(6)
<223> OTHER INFORMATION: 2'fluorocytidine
<220> FEATURE:
<221> NAME/KEY: misc_feature
<222> LOCATION: (9)..(9)
<223> OTHER INFORMATION: n is 2'fluorouridine
<220> FEATURE:
<221> NAME/KEY: modified_base
<222> LOCATION: (12)..(13)
<223> OTHER INFORMATION: 2'fluorocytidine
<220> FEATURE:
<221> NAME/KEY: misc_feature
<222> LOCATION: (14)..(14)
<223> OTHER INFORMATION: n is 2'fluorouridine
<220> FEATURE:
<221> NAME/KEY: modified_base
<222> LOCATION: (15)..(15)
<223> OTHER INFORMATION: 2'fluorocytidine
<220> FEATURE:
<221> NAME/KEY: misc_feature
<222> LOCATION: (18)..(19)
<223> OTHER INFORMATION: n is 2'fluorouridine
<220> FEATURE:
<221> NAME/KEY: modified_base
<222> LOCATION: (20)..(20)
<223> OTHER INFORMATION: 2'fluorocytidine
<220> FEATURE:
<221> NAME/KEY: modified_base
<222> LOCATION: (23)..(23)
<223> OTHER INFORMATION: 2'fluorocytidine
<220> FEATURE:
<221> NAME/KEY: modified_base
<222> LOCATION: (28)..(28)
<223> OTHER INFORMATION: g = dithiophosphate guanine
<220> FEATURE:
<221> NAME/KEY: modified_base
<222> LOCATION: (32)..(32)
<223> OTHER INFORMATION: 2'fluorocytidine
<220> FEATURE:
<221> NAME/KEY: modified_base
<222> LOCATION: (34)..(34)
<223> OTHER INFORMATION: 2'fluorocytidine

<400> SEQUENCE: 7
angancaanc gccncaannc gacaggaggc tcac                              34

<210> SEQ ID NO 8
<211> LENGTH: 34
<212> TYPE: DNA
<213> ORGANISM: Artificial Sequence
<220> FEATURE:
<223> OTHER INFORMATION: Synthetic aptamer
```

```
<220> FEATURE:
<221> NAME/KEY: misc_feature
<222> LOCATION: (2)..(2)
<223> OTHER INFORMATION: n is 2'fluorouridine
<220> FEATURE:
<221> NAME/KEY: misc_feature
<222> LOCATION: (5)..(5)
<223> OTHER INFORMATION: n is 2'fluorouridine
<220> FEATURE:
<221> NAME/KEY: modified_base
<222> LOCATION: (6)..(6)
<223> OTHER INFORMATION: 2'fluorocytidine
<220> FEATURE:
<221> NAME/KEY: misc_feature
<222> LOCATION: (9)..(9)
<223> OTHER INFORMATION: n is 2'fluorouridine
<220> FEATURE:
<221> NAME/KEY: modified_base
<222> LOCATION: (12)..(13)
<223> OTHER INFORMATION: 2'fluorocytidine
<220> FEATURE:
<221> NAME/KEY: misc_feature
<222> LOCATION: (14)..(14)
<223> OTHER INFORMATION: n is 2'fluorouridine
<220> FEATURE:
<221> NAME/KEY: modified_base
<222> LOCATION: (15)..(15)
<223> OTHER INFORMATION: 2'fluorocytidine
<220> FEATURE:
<221> NAME/KEY: misc_feature
<222> LOCATION: (18)..(19)
<223> OTHER INFORMATION: n is 2'fluorouridine
<220> FEATURE:
<221> NAME/KEY: modified_base
<222> LOCATION: (20)..(20)
<223> OTHER INFORMATION: 2'fluorocytidine
<220> FEATURE:
<221> NAME/KEY: modified_base
<222> LOCATION: (23)..(23)
<223> OTHER INFORMATION: 2'fluorocytidine
<220> FEATURE:
<221> NAME/KEY: modified_base
<222> LOCATION: (29)..(29)
<223> OTHER INFORMATION: g = dithiophosphate guanine
<220> FEATURE:
<221> NAME/KEY: modified_base
<222> LOCATION: (32)..(32)
<223> OTHER INFORMATION: 2'fluorocytidine
<220> FEATURE:
<221> NAME/KEY: modified_base
<222> LOCATION: (34)..(34)
<223> OTHER INFORMATION: 2'fluorocytidine

<400> SEQUENCE: 8
angancaanc gccncaannc gacaggaggc tcac                                    34

<210> SEQ ID NO 9
<211> LENGTH: 34
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(1)
<223> OTHER INFORMATION: a = dithiophosphate adenine
<220> FEATURE:
<221> NAME/KEY: misc_feature
<222> LOCATION: (2)..(2)
<223> OTHER INFORMATION: n is 2'fluorouridine
<220> FEATURE:
<221> NAME/KEY: misc_feature
<222> LOCATION: (5)..(5)
<223> OTHER INFORMATION: n is 2'fluorouridine
<220> FEATURE:
<221> NAME/KEY: modified_base
<222> LOCATION: (6)..(6)
```

```
<223> OTHER INFORMATION: 2'fluorocytidine
<220> FEATURE:
<221> NAME/KEY: misc_feature
<222> LOCATION: (9)..(9)
<223> OTHER INFORMATION: n is 2'fluorouridine
<220> FEATURE:
<221> NAME/KEY: modified_base
<222> LOCATION: (12)..(13)
<223> OTHER INFORMATION: 2'fluorocytidine
<220> FEATURE:
<221> NAME/KEY: misc_feature
<222> LOCATION: (14)..(14)
<223> OTHER INFORMATION: n is 2'fluorouridine
<220> FEATURE:
<221> NAME/KEY: modified_base
<222> LOCATION: (15)..(15)
<223> OTHER INFORMATION: 2'fluorocytidine
<220> FEATURE:
<221> NAME/KEY: misc_feature
<222> LOCATION: (18)..(19)
<223> OTHER INFORMATION: n is 2'fluorouridine
<220> FEATURE:
<221> NAME/KEY: modified_base
<222> LOCATION: (20)..(20)
<223> OTHER INFORMATION: 2'fluorocytidine
<220> FEATURE:
<221> NAME/KEY: modified_base
<222> LOCATION: (23)..(23)
<223> OTHER INFORMATION: 2'fluorocytidine
<220> FEATURE:
<221> NAME/KEY: modified_base
<222> LOCATION: (32)..(32)
<223> OTHER INFORMATION: 2'fluorocytidine
<220> FEATURE:
<221> NAME/KEY: modified_base
<222> LOCATION: (34)..(34)
<223> OTHER INFORMATION: 2'fluorocytidine

<400> SEQUENCE: 9
angancaanc gccncaannc gacaggaggc tcac                               34

<210> SEQ ID NO 10
<211> LENGTH: 34
<212> TYPE: DNA
<213> ORGANISM: Artificial Sequence
<220> FEATURE:
<223> OTHER INFORMATION: Synthetic aptamer
<220> FEATURE:
<221> NAME/KEY: misc_feature
<222> LOCATION: (2)..(2)
<223> OTHER INFORMATION: n is 2'fluorouridine
<220> FEATURE:
<221> NAME/KEY: modified_base
<222> LOCATION: (4)..(4)
<223> OTHER INFORMATION: a = dithiophosphate adenine
<220> FEATURE:
<221> NAME/KEY: misc_feature
<222> LOCATION: (5)..(5)
<223> OTHER INFORMATION: n is 2'fluorouridine
<220> FEATURE:
<221> NAME/KEY: modified_base
<222> LOCATION: (6)..(6)
<223> OTHER INFORMATION: 2'fluorocytidine
<220> FEATURE:
<221> NAME/KEY: misc_feature
<222> LOCATION: (9)..(9)
<223> OTHER INFORMATION: n is 2'fluorouridine
<220> FEATURE:
<221> NAME/KEY: modified_base
<222> LOCATION: (12)..(13)
<223> OTHER INFORMATION: 2'fluorocytidine
<220> FEATURE:
<221> NAME/KEY: misc_feature
<222> LOCATION: (14)..(14)
<223> OTHER INFORMATION: n is 2'fluorouridine
<220> FEATURE:
<221> NAME/KEY: modified_base
```

```
<222> LOCATION: (15)..(15)
<223> OTHER INFORMATION: 2'fluorocytidine
<220> FEATURE:
<221> NAME/KEY: misc_feature
<222> LOCATION: (18)..(19)
<223> OTHER INFORMATION: n is 2'fluorouridine
<220> FEATURE:
<221> NAME/KEY: modified_base
<222> LOCATION: (20)..(20)
<223> OTHER INFORMATION: 2'fluorocytidine
<220> FEATURE:
<221> NAME/KEY: modified_base
<222> LOCATION: (23)..(23)
<223> OTHER INFORMATION: 2'fluorocytidine
<220> FEATURE:
<221> NAME/KEY: modified_base
<222> LOCATION: (32)..(32)
<223> OTHER INFORMATION: 2'fluorocytidine
<220> FEATURE:
<221> NAME/KEY: modified_base
<222> LOCATION: (34)..(34)
<223> OTHER INFORMATION: 2'fluorocytidine

<400> SEQUENCE: 10
angancaanc gccncaannc gacaggaggc tcac                                 34

<210> SEQ ID NO 11
<211> LENGTH: 34
<212> TYPE: DNA
<213> ORGANISM: Artificial Sequence
<220> FEATURE:
<223> OTHER INFORMATION: Synthetic aptamer
<220> FEATURE:
<221> NAME/KEY: misc_feature
<222> LOCATION: (2)..(2)
<223> OTHER INFORMATION: n is 2'fluorouridine
<220> FEATURE:
<221> NAME/KEY: misc_feature
<222> LOCATION: (5)..(5)
<223> OTHER INFORMATION: n is 2'fluorouridine
<220> FEATURE:
<221> NAME/KEY: modified_base
<222> LOCATION: (6)..(6)
<223> OTHER INFORMATION: 2'fluorocytidine
<220> FEATURE:
<221> NAME/KEY: modified_base
<222> LOCATION: (7)..(7)
<223> OTHER INFORMATION: a = dithiophosphate adenine
<220> FEATURE:
<221> NAME/KEY: misc_feature
<222> LOCATION: (9)..(9)
<223> OTHER INFORMATION: n is 2'fluorouridine
<220> FEATURE:
<221> NAME/KEY: modified_base
<222> LOCATION: (12)..(13)
<223> OTHER INFORMATION: 2'fluorocytidine
<220> FEATURE:
<221> NAME/KEY: misc_feature
<222> LOCATION: (14)..(14)
<223> OTHER INFORMATION: n is 2'fluorouridine
<220> FEATURE:
<221> NAME/KEY: modified_base
<222> LOCATION: (15)..(15)
<223> OTHER INFORMATION: 2'fluorocytidine
<220> FEATURE:
<221> NAME/KEY: misc_feature
<222> LOCATION: (18)..(19)
<223> OTHER INFORMATION: n is 2'fluorouridine
<220> FEATURE:
<221> NAME/KEY: modified_base
<222> LOCATION: (20)..(20)
<223> OTHER INFORMATION: 2'fluorocytidine
<220> FEATURE:
<221> NAME/KEY: modified_base
<222> LOCATION: (23)..(23)
<223> OTHER INFORMATION: 2'fluorocytidine
<220> FEATURE:
```

```
<221> NAME/KEY: modified_base
<222> LOCATION: (32)..(32)
<223> OTHER INFORMATION: 2'fluorocytidine
<220> FEATURE:
<221> NAME/KEY: modified_base
<222> LOCATION: (34)..(34)
<223> OTHER INFORMATION: 2'fluorocytidine

<400> SEQUENCE: 11
angancaanc gccncaannc gacaggaggc tcac                                34

<210> SEQ ID NO 12
<211> LENGTH: 34
<212> TYPE: DNA
<213> ORGANISM: Artificial Sequence
<220> FEATURE:
<223> OTHER INFORMATION: Synthetic aptamer
<220> FEATURE:
<221> NAME/KEY: misc_feature
<222> LOCATION: (2)..(2)
<223> OTHER INFORMATION: n is 2'fluorouridine
<220> FEATURE:
<221> NAME/KEY: misc_feature
<222> LOCATION: (5)..(5)
<223> OTHER INFORMATION: n is 2'fluorouridine
<220> FEATURE:
<221> NAME/KEY: modified_base
<222> LOCATION: (6)..(6)
<223> OTHER INFORMATION: 2'fluorocytidine
<220> FEATURE:
<221> NAME/KEY: modified_base
<222> LOCATION: (8)..(8)
<223> OTHER INFORMATION: a = dithiophosphate adenine
<220> FEATURE:
<221> NAME/KEY: misc_feature
<222> LOCATION: (9)..(9)
<223> OTHER INFORMATION: n is 2'fluorouridine
<220> FEATURE:
<221> NAME/KEY: modified_base
<222> LOCATION: (12)..(13)
<223> OTHER INFORMATION: 2'fluorocytidine
<220> FEATURE:
<221> NAME/KEY: misc_feature
<222> LOCATION: (14)..(14)
<223> OTHER INFORMATION: n is 2'fluorouridine
<220> FEATURE:
<221> NAME/KEY: modified_base
<222> LOCATION: (15)..(15)
<223> OTHER INFORMATION: 2'fluorocytidine
<220> FEATURE:
<221> NAME/KEY: misc_feature
<222> LOCATION: (18)..(19)
<223> OTHER INFORMATION: n is 2'fluorouridine
<220> FEATURE:
<221> NAME/KEY: modified_base
<222> LOCATION: (20)..(20)
<223> OTHER INFORMATION: 2'fluorocytidine
<220> FEATURE:
<221> NAME/KEY: modified_base
<222> LOCATION: (23)..(23)
<223> OTHER INFORMATION: 2'fluorocytidine
<220> FEATURE:
<221> NAME/KEY: modified_base
<222> LOCATION: (32)..(32)
<223> OTHER INFORMATION: 2'fluorocytidine
<220> FEATURE:
<221> NAME/KEY: modified_base
<222> LOCATION: (34)..(34)
<223> OTHER INFORMATION: 2'fluorocytidine

<400> SEQUENCE: 12
angancaanc gccncaannc gacaggaggc tcac                                34

<210> SEQ ID NO 13
<211> LENGTH: 34
```

<212> TYPE: DNA
<213> ORGANISM: Artificial Sequence
<220> FEATURE:
<223> OTHER INFORMATION: Synthetic aptamer
<220> FEATURE:
<221> NAME/KEY: misc_feature
<222> LOCATION: (2)..(2)
<223> OTHER INFORMATION: n is 2'fluorouridine
<220> FEATURE:
<221> NAME/KEY: misc_feature
<222> LOCATION: (5)..(5)
<223> OTHER INFORMATION: n is 2'fluorouridine
<220> FEATURE:
<221> NAME/KEY: modified_base
<222> LOCATION: (6)..(6)
<223> OTHER INFORMATION: 2'fluorocytidine
<220> FEATURE:
<221> NAME/KEY: misc_feature
<222> LOCATION: (9)..(9)
<223> OTHER INFORMATION: n is 2'fluorouridine
<220> FEATURE:
<221> NAME/KEY: modified_base
<222> LOCATION: (12)..(13)
<223> OTHER INFORMATION: 2'fluorocytidine
<220> FEATURE:
<221> NAME/KEY: misc_feature
<222> LOCATION: (14)..(14)
<223> OTHER INFORMATION: n is 2'fluorouridine
<220> FEATURE:
<221> NAME/KEY: modified_base
<222> LOCATION: (15)..(15)
<223> OTHER INFORMATION: 2'fluorocytidine
<220> FEATURE:
<221> NAME/KEY: modified_base
<222> LOCATION: (16)..(16)
<223> OTHER INFORMATION: a = dithiophosphate adenine
<220> FEATURE:
<221> NAME/KEY: misc_feature
<222> LOCATION: (18)..(19)
<223> OTHER INFORMATION: n is 2'fluorouridine
<220> FEATURE:
<221> NAME/KEY: modified_base
<222> LOCATION: (20)..(20)
<223> OTHER INFORMATION: 2'fluorocytidine
<220> FEATURE:
<221> NAME/KEY: modified_base
<222> LOCATION: (23)..(23)
<223> OTHER INFORMATION: 2'fluorocytidine
<220> FEATURE:
<221> NAME/KEY: modified_base
<222> LOCATION: (32)..(32)
<223> OTHER INFORMATION: 2'fluorocytidine
<220> FEATURE:
<221> NAME/KEY: modified_base
<222> LOCATION: (34)..(34)
<223> OTHER INFORMATION: 2'fluorocytidine

<400> SEQUENCE: 13
angancaanc gccncaannc gacaggaggc tcac                                34

<210> SEQ ID NO 14
<211> LENGTH: 34
<212> TYPE: DNA
<213> ORGANISM: Artificial Sequence
<220> FEATURE:
<223> OTHER INFORMATION: Synthetic aptamer
<220> FEATURE:
<221> NAME/KEY: misc_feature
<222> LOCATION: (2)..(2)
<223> OTHER INFORMATION: n is 2'fluorouridine
<220> FEATURE:
<221> NAME/KEY: misc_feature
<222> LOCATION: (5)..(5)
<223> OTHER INFORMATION: n is 2'fluorouridine
<220> FEATURE:
<221> NAME/KEY: modified_base
<222> LOCATION: (6)..(6)

<223> OTHER INFORMATION: 2'fluorocytidine
<220> FEATURE:
<221> NAME/KEY: misc_feature
<222> LOCATION: (9)..(9)
<223> OTHER INFORMATION: n is 2'fluorouridine
<220> FEATURE:
<221> NAME/KEY: modified_base
<222> LOCATION: (12)..(13)
<223> OTHER INFORMATION: 2'fluorocytidine
<220> FEATURE:
<221> NAME/KEY: misc_feature
<222> LOCATION: (14)..(14)
<223> OTHER INFORMATION: n is 2'fluorouridine
<220> FEATURE:
<221> NAME/KEY: modified_base
<222> LOCATION: (15)..(15)
<223> OTHER INFORMATION: 2'fluorocytidine
<220> FEATURE:
<221> NAME/KEY: modified_base
<222> LOCATION: (17)..(17)
<223> OTHER INFORMATION: a = dithiophosphate adenine
<220> FEATURE:
<221> NAME/KEY: misc_feature
<222> LOCATION: (18)..(19)
<223> OTHER INFORMATION: n is 2'fluorouridine
<220> FEATURE:
<221> NAME/KEY: modified_base
<222> LOCATION: (20)..(20)
<223> OTHER INFORMATION: 2'fluorocytidine
<220> FEATURE:
<221> NAME/KEY: modified_base
<222> LOCATION: (23)..(23)
<223> OTHER INFORMATION: 2'fluorocytidine
<220> FEATURE:
<221> NAME/KEY: modified_base
<222> LOCATION: (32)..(32)
<223> OTHER INFORMATION: 2'fluorocytidine
<220> FEATURE:
<221> NAME/KEY: modified_base
<222> LOCATION: (34)..(34)
<223> OTHER INFORMATION: 2'fluorocytidine

<400> SEQUENCE: 14
angancaanc gccncaannc gacaggaggc tcac                          34

<210> SEQ ID NO 15
<211> LENGTH: 34
<212> TYPE: DNA
<213> ORGANISM: Artificial Sequence
<220> FEATURE:
<223> OTHER INFORMATION: Synthetic aptamer
<220> FEATURE:
<221> NAME/KEY: misc_feature
<222> LOCATION: (2)..(2)
<223> OTHER INFORMATION: n is 2'fluorouridine
<220> FEATURE:
<221> NAME/KEY: misc_feature
<222> LOCATION: (5)..(5)
<223> OTHER INFORMATION: n is 2'fluorouridine
<220> FEATURE:
<221> NAME/KEY: modified_base
<222> LOCATION: (6)..(6)
<223> OTHER INFORMATION: 2'fluorocytidine
<220> FEATURE:
<221> NAME/KEY: misc_feature
<222> LOCATION: (9)..(9)
<223> OTHER INFORMATION: n is 2'fluorouridine
<220> FEATURE:
<221> NAME/KEY: modified_base
<222> LOCATION: (12)..(13)
<223> OTHER INFORMATION: 2'fluorocytidine
<220> FEATURE:
<221> NAME/KEY: misc_feature
<222> LOCATION: (14)..(14)
<223> OTHER INFORMATION: n is 2'fluorouridine
<220> FEATURE:
<221> NAME/KEY: modified_base -continued

```
<222> LOCATION: (15)..(15)
<223> OTHER INFORMATION: 2'fluorocytidine
<220> FEATURE:
<221> NAME/KEY: misc_feature
<222> LOCATION: (18)..(19)
<223> OTHER INFORMATION: n is 2'fluorouridine
<220> FEATURE:
<221> NAME/KEY: modified_base
<222> LOCATION: (20)..(20)
<223> OTHER INFORMATION: 2'fluorocytidine
<220> FEATURE:
<221> NAME/KEY: modified_base
<222> LOCATION: (22)..(22)
<223> OTHER INFORMATION: a = dithiophosphate adenine
<220> FEATURE:
<221> NAME/KEY: modified_base
<222> LOCATION: (23)..(23)
<223> OTHER INFORMATION: 2'fluorocytidine
<220> FEATURE:
<221> NAME/KEY: modified_base
<222> LOCATION: (32)..(32)
<223> OTHER INFORMATION: 2'fluorocytidine
<220> FEATURE:
<221> NAME/KEY: modified_base
<222> LOCATION: (34)..(34)
<223> OTHER INFORMATION: 2'fluorocytidine

<400> SEQUENCE: 15
angancaanc gccncaannc gacaggaggc tcac                               34

<210> SEQ ID NO 16
<211> LENGTH: 34
<212> TYPE: DNA
<213> ORGANISM: Artificial Sequence
<220> FEATURE:
<223> OTHER INFORMATION: Synthetic aptamer
<220> FEATURE:
<221> NAME/KEY: misc_feature
<222> LOCATION: (2)..(2)
<223> OTHER INFORMATION: n is 2'fluorouridine
<220> FEATURE:
<221> NAME/KEY: misc_feature
<222> LOCATION: (5)..(5)
<223> OTHER INFORMATION: n is 2'fluorouridine
<220> FEATURE:
<221> NAME/KEY: modified_base
<222> LOCATION: (6)..(6)
<223> OTHER INFORMATION: 2'fluorocytidine
<220> FEATURE:
<221> NAME/KEY: misc_feature
<222> LOCATION: (9)..(9)
<223> OTHER INFORMATION: n is 2'fluorouridine
<220> FEATURE:
<221> NAME/KEY: modified_base
<222> LOCATION: (12)..(13)
<223> OTHER INFORMATION: 2'fluorocytidine
<220> FEATURE:
<221> NAME/KEY: misc_feature
<222> LOCATION: (14)..(14)
<223> OTHER INFORMATION: n is 2'fluorouridine
<220> FEATURE:
<221> NAME/KEY: modified_base
<222> LOCATION: (15)..(15)
<223> OTHER INFORMATION: 2'fluorocytidine
<220> FEATURE:
<221> NAME/KEY: misc_feature
<222> LOCATION: (18)..(19)
<223> OTHER INFORMATION: n is 2'fluorouridine
<220> FEATURE:
<221> NAME/KEY: modified_base
<222> LOCATION: (20)..(20)
<223> OTHER INFORMATION: 2'fluorocytidine
<220> FEATURE:
<221> NAME/KEY: modified_base
<222> LOCATION: (23)..(23)
<223> OTHER INFORMATION: 2'fluorocytidine
<220> FEATURE:
```

```
<221> NAME/KEY: modified_base
<222> LOCATION: (24)..(24)
<223> OTHER INFORMATION: a = dithiophosphate adenine
<220> FEATURE:
<221> NAME/KEY: modified_base
<222> LOCATION: (32)..(32)
<223> OTHER INFORMATION: 2'fluorocytidine
<220> FEATURE:
<221> NAME/KEY: modified_base
<222> LOCATION: (34)..(34)
<223> OTHER INFORMATION: 2'fluorocytidine

<400> SEQUENCE: 16
angancaanc gccncaannc gacaggaggc tcac                                34

<210> SEQ ID NO 17
<211> LENGTH: 34
<212> TYPE: DNA
<213> ORGANISM: Artificial Sequence
<220> FEATURE:
<223> OTHER INFORMATION: Synthetic aptamer
<220> FEATURE:
<221> NAME/KEY: misc_feature
<222> LOCATION: (2)..(2)
<223> OTHER INFORMATION: n is 2'fluorouridine
<220> FEATURE:
<221> NAME/KEY: misc_feature
<222> LOCATION: (5)..(5)
<223> OTHER INFORMATION: n is 2'fluorouridine
<220> FEATURE:
<221> NAME/KEY: modified_base
<222> LOCATION: (6)..(6)
<223> OTHER INFORMATION: 2'fluorocytidine
<220> FEATURE:
<221> NAME/KEY: misc_feature
<222> LOCATION: (9)..(9)
<223> OTHER INFORMATION: n is 2'fluorouridine
<220> FEATURE:
<221> NAME/KEY: modified_base
<222> LOCATION: (12)..(13)
<223> OTHER INFORMATION: 2'fluorocytidine
<220> FEATURE:
<221> NAME/KEY: misc_feature
<222> LOCATION: (14)..(14)
<223> OTHER INFORMATION: n is 2'fluorouridine
<220> FEATURE:
<221> NAME/KEY: modified_base
<222> LOCATION: (15)..(15)
<223> OTHER INFORMATION: 2'fluorocytidine
<220> FEATURE:
<221> NAME/KEY: misc_feature
<222> LOCATION: (18)..(19)
<223> OTHER INFORMATION: n is 2'fluorouridine
<220> FEATURE:
<221> NAME/KEY: modified_base
<222> LOCATION: (20)..(20)
<223> OTHER INFORMATION: 2'fluorocytidine
<220> FEATURE:
<221> NAME/KEY: modified_base
<222> LOCATION: (23)..(23)
<223> OTHER INFORMATION: 2'fluorocytidine
<220> FEATURE:
<221> NAME/KEY: modified_base
<222> LOCATION: (27)..(27)
<223> OTHER INFORMATION: a = dithiophosphate adenine
<220> FEATURE:
<221> NAME/KEY: modified_base
<222> LOCATION: (32)..(32)
<223> OTHER INFORMATION: 2'fluorocytidine
<220> FEATURE:
<221> NAME/KEY: modified_base
<222> LOCATION: (34)..(34)
<223> OTHER INFORMATION: 2'fluorocytidine

<400> SEQUENCE: 17
angancaanc gccncaannc gacaggaggc tcac                                34
```

<210> SEQ ID NO 18
<211> LENGTH: 34
<212> TYPE: DNA
<213> ORGANISM: Artificial Sequence
<220> FEATURE:
<223> OTHER INFORMATION: Synthetic aptamer
<220> FEATURE:
<221> NAME/KEY: misc_feature
<222> LOCATION: (2)..(2)
<223> OTHER INFORMATION: n is 2'fluorouridine
<220> FEATURE:
<221> NAME/KEY: misc_feature
<222> LOCATION: (5)..(5)
<223> OTHER INFORMATION: n is 2'fluorouridine
<220> FEATURE:
<221> NAME/KEY: modified_base
<222> LOCATION: (6)..(6)
<223> OTHER INFORMATION: 2'fluorocytidine
<220> FEATURE:
<221> NAME/KEY: misc_feature
<222> LOCATION: (9)..(9)
<223> OTHER INFORMATION: n is 2'fluorouridine
<220> FEATURE:
<221> NAME/KEY: modified_base
<222> LOCATION: (12)..(13)
<223> OTHER INFORMATION: 2'fluorocytidine
<220> FEATURE:
<221> NAME/KEY: misc_feature
<222> LOCATION: (14)..(14)
<223> OTHER INFORMATION: n is 2'fluorouridine
<220> FEATURE:
<221> NAME/KEY: modified_base
<222> LOCATION: (15)..(15)
<223> OTHER INFORMATION: 2'fluorocytidine
<220> FEATURE:
<221> NAME/KEY: misc_feature
<222> LOCATION: (18)..(19)
<223> OTHER INFORMATION: n is 2'fluorouridine
<220> FEATURE:
<221> NAME/KEY: modified_base
<222> LOCATION: (20)..(20)
<223> OTHER INFORMATION: 2'fluorocytidine
<220> FEATURE:
<221> NAME/KEY: modified_base
<222> LOCATION: (23)..(23)
<223> OTHER INFORMATION: 2'fluorocytidine
<220> FEATURE:
<221> NAME/KEY: modified_base
<222> LOCATION: (32)..(32)
<223> OTHER INFORMATION: 2'fluorocytidine
<220> FEATURE:
<221> NAME/KEY: modified_base
<222> LOCATION: (33)..(33)
<223> OTHER INFORMATION: a = dithiophosphate adenine
<220> FEATURE:
<221> NAME/KEY: modified_base
<222> LOCATION: (34)..(34)
<223> OTHER INFORMATION: 2'fluorocytidine

<400> SEQUENCE: 18
angancaanc gccncaannc gacaggaggc tcac                               34

<210> SEQ ID NO 19
<211> LENGTH: 34
<212> TYPE: RNA
<213> ORGANISM: Artificial Sequence
<220> FEATURE:
<223> OTHER INFORMATION: Synthetic aptamer

<400> SEQUENCE: 19
augaucaauc gccucaauuc gacaggaggc ucac                               34

<210> SEQ ID NO 20

```
<211> LENGTH: 34
<212> TYPE: DNA
<213> ORGANISM: Artificial Sequence
<220> FEATURE:
<223> OTHER INFORMATION: Synthetic aptamer

<400> SEQUENCE: 20
atgatcaatc gcctcaattc gacaggaggc tcac                             34
```

DNA APTAMERS AND USE THEREOF FOR THE TREATMENT OF CANCER

This application is a national phase application under 35 U.S.C. § 371 of International Application No. PCT/US2019/066654, filed Dec. 16, 2019, which claims the benefit of U.S. Provisional Application No. 62/780,058, filed Dec. 14, 2018, the entirety of each of which is incorporated herein by reference.

This invention was made with government support under grant number CA213759 awarded by the National Institutes of Health. The government has certain rights in the invention.

INCORPORATION OF SEQUENCE LISTING

The sequence listing that is contained in the file named "UTSCP1400US_ST25.txt", which is 21,972 bytes (as measured in Microsoft Windows®) and was created on Mar. 21, 2024, is filed herewith by electronic submission and is incorporated by reference herein.

BACKGROUND

1. Field

The present invention relates generally to the fields of immunology and medicine. More particularly, it concerns DNA aptamers and use thereof.

2. Description of Related Art

AXL, receptor tyrosine kinase (RTK), is a transmembrane protein along with its homologues Tyro3 and Mer, in the Tyro3-Axl-Mer (TAM) receptor kinase subfamily. Its extracellular domain is composed of two immunoglobulin-like (Ig) domains and two fibronectin type 3-like domains. AXL receptor functions as a sensor for extracellular ligands. The activation mechanisms involve the stimulation of the extracellular domain of the receptor with bridging protein ligands. The main ligand of AXL is growth arrest-specific protein 6 (Gas 6), a γ-carboxylated protein, that binds AXL receptor with high affinity inducing the dimerization and autophosphorylation of tyrosine residues which leads to recruitment, phosphorylation and activation of several downstream proteins involved in the regulation of survival, growth, differentiation, adhesion, proliferation, and motility. AXL is ubiquitously expressed including in a wide range of organs and cells including monocytes, macrophages, endothelial cells, heart, skeletal muscles, liver and kidney.

The overexpression or increase in activity of Gas 6/AXL interaction has been reported in many human cancers such as colon, esophageal, thyroid, breast, lung, liver, ovarian and astrocytoma-glioblastoma and has been associated with poor prognosis. Epithelial ovarian cancer (EOC) is the most lethal gynecological malignancy. AXL is known to be over-expressed in advanced EOC, particularly in tumors that have metastasized. Experimental evidence has demonstrated that patients expressing high levels of AXL have shorter over-survival than patients expressing low levels of AXL in EOC. Therefore, there is an unmet need for novel strategies for silencing and blocking this signaling pathway and the dissemination of ovarian cancer.

SUMMARY

In a first embodiment, the present disclosure provides for a new method to treat a variety of diseases including cancer, infectious diseases, autoimmune diseases by selectively targeting the disease-causing cells or organisms.

In one embodiment, there are provided DNA aptamers comprising a thiophosphate backbone, such as a monothiophosphate or dithiophosphate backbone, which selectively bind to AXL receptor kinase. In particular aspects, the aptamer reduces AXL expression, activity, and/or phosphorylation.

In some aspects, the DNA aptamer has a sequence with at least 90%, 91%, 92%, 93%, 94%, 95%, 96%, 97%, 98%, or 99% identity to SEQ ID NO:1. In some aspects, the DNA aptamer has the sequence of SEQ ID NO:1. In certain aspects, the aptamer is 40-100 nucleotides in length, such as 40, 45, 50, 55, 60, 65, 70, 75, 80, 85, 90, 95, or 100 nucleotides in length. In other aspects, the aptamer is 20-40 nucleotides in length, such as 39, 38, 37, 36, 35, 34, 33, 32, 31, 30, 29, 28, 27, 26, or 25 nucleotides in length. In specific aspects, the aptamer has a length of 34 nucleotides.

In particular aspects, the dithiophosphate (or monothiophosphate) backbone is at position 25 of SEQ ID NO:1. In some aspects, the dithiophosphate (or monothiophosphate) backbone is at position 4 of SEQ ID NO:1.

In certain aspects, at least one nucleotide is chemically modified with 2'-fluoropyrimidine. In particular aspects, 2, 3, 4, or 5 pyrimidines are chemically modified with 2'-fluoropyrimidine. In some aspects, all of the pyrimidines are chemically modified with 2'-fluoro pyrimidine.

In further aspects, the aptamer is polyethylene glycol (PEG) modified. In some aspects, the PEG is conjugated to the 5' end of the aptamer. In other aspects, the PEG is conjugated to the 3' end of the aptamer. The PEG may be conjugated to both ends of the aptamer. In particular aspects, the PEG is maleimide PEG which may have a molecular weight of 10 kilodalton.

In some aspects, the aptamer is single-stranded. In particular aspects, the aptamer folds into a hairpin-like structure which can comprise a loop region, a stem region, and two single-stranded ends.

In particular aspects, the aptamer comprises at least one 2'-fluoropyrimidine modified nucleotide and is PEG-modified. For example, the aptamer is GLB-25 or GLB-A04, as depicted in FIG. 6.

In certain aspects, the aptamer is stable is serum for more than 24 hours, such as for 36 hours, 48 hours, 72 hours, or 96 hours.

In additional aspects, the aptamer further comprises a detectable label.

In particular aspects, the aptamer has increased stability, or increased function, as compared to a DNA aptamer with a monothiophosphate backbone or without 2'-fluoro pyrimidine or PEGylation.

Further provided herein is a pharmaceutical composition comprising an AXL DNA aptamer of the embodiments and a pharmaceutically acceptable carrier. The composition can further comprise a chemotherapeutic, such as paclitaxel or cisplatin.

In another embodiment, there is provided a composition comprising an effective amount of an AXL DNA aptamer of the embodiments for use in the treatment of a disease or disorder in a subject. In some aspects, the disease or disorder is cancer, an infectious disease, or an autoimmune disease. The composition can further comprise a chemotherapeutic, such as paclitaxel or cisplatin.

A further embodiment provides the use of a composition comprising an AXL DNA aptamer of the embodiments for the treatment of a disease or disorder in a subject. In some aspects, the disease or disorder is cancer, an infectious disease, or an autoimmune disease. The composition can further comprise a chemotherapeutic, such as paclitaxel or cisplatin.

Another embodiment provides a method of treating a disease or disorder in a subject comprising administering an effective amount of a DNA aptamer of the embodiments to the subject. In some aspects, the disease or disorder is cancer, an infectious disease, or an autoimmune disease. In particular aspects, the subject is human.

In some aspects of the above embodiments, the infectious disease is caused by a virus, mycobacteria, bacteria, or fungus. In certain aspects, the cancer is breast cancer, colon cancer, prostate cancer, lung cancer, gastric cancer, ovarian cancer, endometrial cancer, renal cancer, hepatocellular cancer, thyroid cancer, uterine cancer, esophageal carcinoma, squamous cell carcinoma, leukemia, osteosarcoma, melanoma, glioblastoma or neuroblastoma. In particular aspects, the cancer is ovarian cancer, such as metastatic ovarian cancer.

In certain aspects, the subject is further administered a chemotherapy. In specific aspects, the chemotherapy is paclitaxel or cisplatin. The DNA aptamer can result in increased efficacy of the chemotherapy, such as paclitaxel. In some aspects, the DNA aptamer results in decreased migration and/or invasion of cancer cells. In certain aspects, the DNA aptamer inhibits tumor growth and/or metastatic nodules. In some aspects, the DNA aptamer is administered intravenously.

In additional aspects, the method further comprises administering at least a second therapeutic agent, such as an intervention. In some aspects, the at least a second therapeutic agent comprises chemotherapy, immunotherapy, surgery, radiotherapy, or biotherapy. In particular aspects, the at least a second therapeutic agent is administered intravenously, intraperitoneally, intratracheally, intratumorally, intramuscularly, endoscopically, intralesionally, percutaneously, subcutaneously, regionally, or by direct injection or perfusion.

Further provided herein is a method for the detection of AXL receptor kinase comprising: (a) incubating a sample with a DNA aptamer of the embodiments; and (b) measuring the binding of the DNA aptamer to the sample. In some aspects, the sample is blood, serum, saliva, biopsy, urine, or cerebrospinal fluid.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 3A-3D: Dithiophosphate and polyethylene glycol modifications prolong stability in human serum, PK profile and biodistribution in vivo. (A) Stability in human serum: Stability of up to 72 hours for GLB-G25 and GLB-A04 aptamers in human serum far exceeds previously reported stability values of 6 hours for GL21.T and 24 hours for GLD-1 (B) Pharmacokinetics profile for GLB-G25 PEG (C) Pharmacokinetics profile for GLB-G25 and GLB-A04 PEG: PEG modified GLB-G25 and GLB-A04 aptamers were retained (bioavailability) at 10 µg/mL after 500 min (D) Ex vivo tumor, kidney, spleen, liver, lung, heart, brain penetration analysis shows the higher penetration of the PEG-modified GLB-G25 (left image lane 1, rows 7-9) and GLB-A04 (right image lane 1; rows 7-9) into the tumor compared to untreated (right image lane 1; rows 1-3) and PEG alone (left image lane 1; rows 1-3). It is expected that in general the aptamer whether modified or not would penetrate other organs but not heart and brain.

FIGS. 6A-6C: Design, screening and selection of dithiophosphate modified candidates GLB-G25 and GLB-A04 based on inhibition of p-AXL expression in HeyA8 ovarian cancer cell line. (A) Modifications table of 17 dithiophosphate modified DNA aptamers. (B) Selection of GLB-G25 and GLB-A04 in HeyA8 ovarian cancer cell line, based on p-AXL expression following Gas 6 ligand treatment. (C) Secondary structure of GL21.T and GLB-25 and GLB-A04 by Mfold software.

DESCRIPTION OF ILLUSTRATIVE EMBODIMENTS

Figure 1:
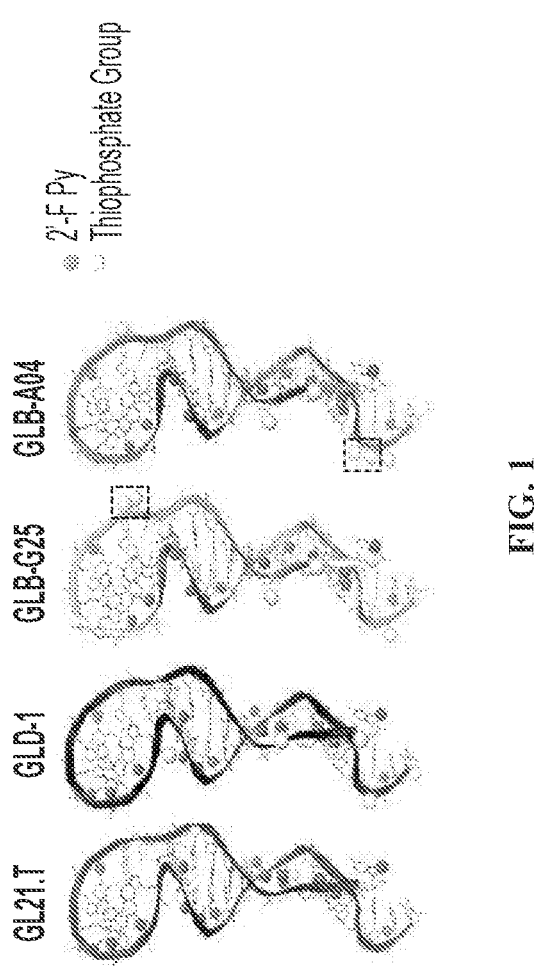
FIG. 1: The addition of dithiophosphate modifications do not have any effect on the 3D structure of GL21.T, GLD-1, GLB-G25 and GLB-A04. The present designs of GLB-G25 and GLB-A04 do not change the 3D structure. The boxed modifications are thiophosphate groups.

Nucleic acid molecules, called aptamers, show high specificity and safety and hence have been used to design therapeutics for several cancer targets. Aptamers comprise synthetic single strand of DNA or RNA oligonucleotides. Aptamers designed and selected through repeated rounds of in vitro selection called Systematic Evolution of Ligands by Exponential Enrichment (SELEX) are highly specific in binding to their target (e.g., proteins, nucleic acids, small molecules, or cells) through non-covalent interactions (e.g., electrostatic, hydrophobic and three-dimensional structural interactions). In essence, aptamers can be "synthetic antibodies" that act like monoclonal antibodies and bind to the target with high specificity and affinity and unlike antibodies, aptamers show little or no immunogenic effects. Aptamers can be conjugated with other molecules to increase their effectiveness. The small size and chemical flexibility of aptamers leads to more efficient penetration of tissue barriers. Aptamers have been used as tools for several therapeutic approaches such as biosensing, drug delivery and theranostic applications. However, problems with aptamers may include aptamer degradation by nucleases, specifically RNA aptamers, aptamer removal by renal filtration, bioavailability for action, delivery into cells, and cross-reactivity.

Thus, in certain embodiments, the present disclosure provides DNA aptamers targeting AXL receptor. The present DNA aptamers can have decreased nuclease hydrolysis and renal clearance due to improved stability in vivo. The present DNA aptamers can have a monothiophosphate or dithiophosphate backbone, 2-fluoro-pyrimidine, and/or polyethylene glycol (PEG) modification. Specifically, the DNA aptamer may be chemically modified to comprise dithiophosphate backbone, 2-fluoro-pyrimidine, and PEG modifications, referred to herein as a 2FT-PEGamer. The DNA aptamer may have the sequence ATGATCAATCGCCTCAATTCGACAGGAGGCTCAC (SEQ ID NO:1) or a sequence with at least 90%, 91%, 92%, 93%, 94%, 95%, 96%, 97%, 98%, or 99% identity or similarity to SEQ ID NO:1.

Further provided herein are methods of treating cancer, such as ovarian cancer, particularly metastatic and advanced ovarian cancer, comprising administering the present DNA aptamer. The present studied evaluated the in vitro and in vivo antitumor activity of the DNA aptamer using in vitro assays as well as two intraperitoneal animal models. The therapeutic 2FT-PEGamer treatment inhibited the phosphorylation and the activity of AXL, impaired the migration and invasion ability of ovarian cancer cells, and led to the inhibition of tumor growth and number of intraperitoneal metastatic nodules, which was associated with the inhibition of AXL activity and angiogenesis in tumors. When combined with paclitaxel, in vivo systemic (e.g., intravenous [i.v.]) administration of 2FT-PEGamer treatment markedly enhanced the antitumor efficacy of paclitaxel in mice. Taken together, the data indicated that 2FT-PEGamer successfully targeted in vivo AXL-RTK and inhibited its AXL activity and tumor growth and progression, representing a promising strategy for the treatment of ovarian cancer.

I. DEFINITIONS

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more. The terms "about", "substantially" and "approximately" mean, in general, the stated value plus or minus 5%.

"Treating" or treatment of a disease or condition refers to executing a protocol, which may include administering one or more drugs to a patient, in an effort to alleviate signs or symptoms of the disease. Desirable effects of treatment include decreasing the rate of disease progression, ameliorating or palliating the disease state, and remission or improved prognosis. Alleviation can occur prior to signs or symptoms of the disease or condition appearing, as well as after their appearance. Thus, "treating" or "treatment" may include "preventing" or "prevention" of disease or undesirable condition. In addition, "treating" or "treatment" does not require complete alleviation of signs or symptoms, does not require a cure, and specifically includes protocols that have only a marginal effect on the patient.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease. For example, treatment of cancer may involve, for example, a reduction in the size of a tumor, a reduction in the invasiveness of a tumor, reduction in the growth rate of the cancer, or prevention of metastasis. Treatment of cancer may also refer to prolonging survival of a subject with cancer.

"Subject" and "patient" refer to either a human or non-human, such as primates, mammals, and vertebrates. In particular embodiments, the subject is a human.

The phrases "pharmaceutical or pharmacologically acceptable" refers to molecular entities and compositions that do not produce an adverse, allergic, or other untoward reaction when administered to an animal, such as a human, as appropriate. The preparation of a pharmaceutical composition comprising an antibody or additional active ingredient will be known to those of skill in the art in light of the present disclosure. Moreover, for animal (e.g., human) administration, it will be understood that preparations should meet sterility, pyrogenicity, general safety, and purity standards as required by FDA Office of Biological Standards.

As used herein, "pharmaceutically acceptable carrier" includes any and all aqueous solvents (e.g., water, alcoholic/aqueous solutions, saline solutions, parenteral vehicles, such as sodium chloride, Ringer's dextrose, etc.), non-aqueous solvents (e.g., propylene glycol, polyethylene glycol, vegetable oil, and injectable organic esters, such as ethyloleate), dispersion media, coatings, surfactants, antioxidants, preservatives (e.g., antibacterial or antifungal agents, anti-oxidants, chelating agents, and inert gases), isotonic agents, absorption delaying agents, salts, drugs, drug stabilizers, gels, binders, excipients, disintegration agents, lubricants, sweetening agents, flavoring agents, dyes, fluid and nutrient replenishers, such like materials and combinations thereof, as would be known to one of ordinary skill in the art. The pH and exact concentration of the various components in a pharmaceutical composition are adjusted according to well-known parameters.

The indication of an identity of nucleotide or amino acid sequences in conjunction with a percentage, say "x % identity" refers to a comparison of two sequences, where in each case a position in the compared a sequence with the corresponding position in the other sequence, and means an identity of the nucleotides or amino acids of the two sequences being compared in x % of positions compared. It may be necessary to consider sequence gaps to make the best possible Alinierung of comparison sequences. Identity is therefore that the comparison of two sequences at equivalent sites in each case the same nucleotide or amino acid is the same. The degree of similarity or identity of two sequences (for example, using the computer program BLAST) are determined using standard parameters, the skilled person is familiar, which program is suitable for the particular sequence (for example, for nucleotide BLASTn, BLASTp for amino acid sequences).

II. DNA APTAMERS

DNA oligonucleotides (ODNs) can act as "aptamers," as direct in vivo inhibitors selected from combinatorial libraries. A DNA aptamer may be an isolated single-stranded DNA (ssDNA) that specifically binds a target molecule, such as a protein, particularly AXL receptor kinase. In particular, ssDNA oligonucleotides may be 15-100 nucleotides in length, such as at most 150, preferably at most 130, at most 110, at most 100, at most 90, at most 80, at most 70, at most 60, at most 50, at most 40, at most 30, at most 20, at most 15 or at most 10 nucleotides. The DNA aptamer may preferably be less than 40 nucleotides in length, such as 39, 38, 37, 36, 35, 34, 33, or 33 nucleotides in length, particularly 34 nucleotides in length.

The DNA aptamer can have a sequence according to SEQ ID NO: 1, such as no further nucleotides at the 3' and 5' ends of the sequence. One or more, possibly all bases of the nucleotides of the DNA aptamer may be modified. This may be advantageous in order to reduce, for example, the sensitivity to nucleases in vivo, to improve the uptake into the cell or to prevent rapid renal absorption. To protect from attack by exonucleases, for example at the 3'-end, the aptamer may comprise a 3"dT cap.

The DNA aptamer can comprise polyethylene glycol (PEG) and/or cholesterol to increase, for example, the bioavailability or the affinity to reduce the degradation or excretion. Thus, the DNA aptamer may be PEGylated. "PEGylated" means that the DNA aptamer is conjugated to a polyethylene glycol (PEG) polymer. The PEG may be a linear PEG polymer of 10 kDa, 20 kDa, 30 kDa or 40 kDa or may be a branched PEG polymer.

For conjugation of thioaptamers with PEG, such as 10-kd PEG, approximately 100 nmole of HPLC-purified C6SS thiol-modified thioaptamer may be suspended in 500 μl phosphate-buffered saline (PBS) with pH 7.4 and reduced with 20 μM DTT for 1 hour. DTT may be removed by filtration through 3-kd spin filters. Reduced thioaptamers can be incubated with 3-fold molar excess of monofunctionalized PEG, such as 10K PEG-maleimide (Creative PEG Works, Durham, NC, USA) for 3 hours. After the reaction, the mixture may be filtered to 10-kd cutoff spin filters to remove unreacted PEG, such as PEG-maleimide. The efficiency of PEGylation may be monitored by mobility shift on polyacrylamide gel.

The DNA nucleotide aptamer may have at least one or all of the pyrimidine residues modified to 2'-fluoropyrimidines. The pyrimidine residues may also be modified as 2'-O-alkyl nucleotides, as 3' end cap and locked nucleic acids, or as LNA modifications to significantly enhance stability.

As used herein, "thiophosphate" refers to analogs of DNA or RNA having sulphur in place of one or more of the non-bridging oxygens bound to the phosphorus. Monothiophosphates or phosphoromonothioates [αS] have only one sulfur and are thus chiral around the phosphorus center. Dithiophosphates are substituted at both oxygens and are thus achiral. Phosphoromonothioate nucleotides are commercially available or can be synthesized by several different methods known in the art.

When discussing changes to oligonucleotides, "modified" is used herein to describe oligonucleotides or libraries in which one or more of the four constituent nucleotide bases of an oligonucleotide are analogues or esters of nucleotides normally comprising DNA or RNA backbones and wherein such modification confers increased nuclease resistance. Thiophosphate nucleotides are an example of modified nucleotides.

Aptamers can be synthesized on an Expedite 8909 Oligo Synthesizer (Applied Biosystems) using standard phosphoramidite chemistry. Standard DNA synthesis reagents, Cy3-phosphoramidite, 5'-biotinTEG phosphoramidite, and Sulfurizing Reagent II may be purchased from Glen Research. 2'-fluoro-dC and 2'-fluoro-dU phosphoramidites were purchased from both Glen Research and from Sigma-Aldrich. Aptamers may be deprotected in concentrated ammonium hydroxide overnight at room temperature, vacuum dried overnight, and purified by reverse-phase chromatography over a Hamilton PRP-1 column on an AKTA 10 purifier (General Electric), by loading using a 100 mM triethylamine acetate buffer (pH 8.4) and eluting with increasing acetonitrile concentrations. Aptamer concentrations can be determined using extinction coefficients estimated by OligoCalc. To promote the formation of ideal secondary structure, the aptamer may be subjected to a denaturing step (85° C. for 5 min, followed by incubation on ice for 2 min and at 37° C. for 10 min) individually to promote the formation of ideal secondary structure.

The present aptamers may have one or more detectable labels. "Detectable labels" are compounds and/or elements that can be detected due to their specific functional properties and/or chemical characteristics, the use of which allows the agent to which they are attached to be detected, and/or further quantified if desired, such as, e.g., an enzyme, an antibody, a linker, a radioisotope, an electron dense particle, a magnetic particle and/or a chromophore or combinations thereof, e.g., fluorescence resonance energy transfer (FRET). There are many types of detectable labels, including fluorescent labels, which are easily handled, inexpensive and nontoxic.

The DNA aptamer may be modified by the addition of other substances, such as an amino acid, a peptide, inverted dT, a lipid, a dye, a fluorescent substance, an enzyme, a radioactive substance, and biotin. Such substance may be linked via a known linker, if needed. Examples of linkers used herein include a nucleotide linker, a peptide linker, and a linker containing a disulfide bond.

III. METHODS OF TREATMENT

In further embodiments, the present disclosure provides methods for the treatment of hyperproliferative disorders, infectious diseases, or autoimmune diseases with the administration of an effective amount of the present DNA aptamers. The disorder may be cancer, such as breast cancer, colon cancer, prostate cancer, lung cancer, gastric cancer, ovarian cancer, endometrial cancer, renal cancer, hepatocellular cancer, thyroid cancer, uterine cancer, esophageal carcinoma, squamous cell carcinoma, leukemia, osteosarcoma, melanoma, glioblastoma, neuroblastoma, or primary tumor metastasis.

Tumors for which the present treatment methods are useful include any malignant cell type, such as those found in a solid tumor or a hematological tumor. Exemplary solid tumors can include, but are not limited to, a tumor of an organ selected from the group consisting of pancreas, colon, cecum, stomach, brain, head, neck, ovary, kidney, larynx, sarcoma, lung, bladder, melanoma, prostate, and breast. Exemplary hematological tumors include tumors of the bone marrow, T or B cell malignancies, leukemias, lymphomas, blastomas, myelomas, and the like. Further examples of cancers that may be treated using the methods provided herein include, but are not limited to, lung cancer (including small-cell lung cancer, non-small cell lung cancer, adenocarcinoma of the lung, and squamous carcinoma of the lung), cancer of the peritoneum, gastric or stomach cancer (including gastrointestinal cancer and gastrointestinal stromal cancer), pancreatic cancer, cervical cancer, ovarian cancer, liver cancer, bladder cancer, breast cancer, colon cancer, colorectal cancer, endometrial or uterine carcinoma, salivary gland carcinoma, kidney or renal cancer, prostate cancer, vulval cancer, thyroid cancer, various types of head and neck cancer, and melanoma.

The cancer may specifically be of the following histological type, though it is not limited to these: neoplasm, malignant: carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant: sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; lentigo malignant melanoma; acral lentiginous melanomas: nodular melanomas; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant: struma ovarii, malignant; choriocarcinoma; mesonephroma, malignant; hemangiosarcoma: hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pincaloma, malignant; chordoma; glioma, malignant: ependymoma; astrocytoma; protoplasmic astrocytoma: fibrillary astrocytoma; astroblastoma: glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease: hodgkin's; paragranuloma: malignant lymphoma, small lymphocytic; malignant lymphoma, large cell, diffuse, malignant lymphoma, follicular; mycosis fungoides; other specified non-hodgkin's lymphomas: B-cell lymphoma; low grade/follicular non-Hodgkin's lymphoma (NHL); small lymphocytic (SL) NHL; intermediate grade/follicular NHL: intermediate grade diffuse NHL; high grade immunoblastic NHL; high grade lymphoblastic NHL; high grade small non-cleaved cell NHL: bulky disease NHL: mantle cell lymphoma; AIDS-related lymphoma; Waldenstrom's macroglobulinemia; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; hairy cell leukemia; chronic lymphocytic leukemia (CLL); acute lymphoblastic leukemia (ALL); acute myeloid leukemia (AML); and chronic myeloblastic leukemia.

Therapeutically effective amounts of DNA aptamers can be administered by a number of routes, including parenteral administration, for example, intravenous, intraperitoneal, intramuscular, intrasternal, or intraarticular injection, or infusion. In particular embodiments, the DNA aptamers are administered intravenously.

The therapeutically effective amount of DNA aptamers for use in adoptive cell therapy is that amount that achieves a desired effect in a subject being treated. For instance, this can be the amount of DNA aptamer necessary to inhibit advancement, or to cause regression of a cancer, or which is capable of relieving symptoms caused by cancer.

The DNA aptamer can be administered in treatment regimens consistent with the disease, for example a single or a few doses over one to several days to ameliorate a disease state or periodic doses over an extended time to inhibit disease progression and prevent disease recurrence. The precise dose to be employed in the formulation will also depend on the route of administration, and the seriousness of the disease or disorder, and should be decided according to the judgment of the practitioner and each patient's circumstances. The therapeutically effective amount of DNA aptamer will be dependent on the subject being treated, the severity and type of the affliction, and the manner of administration. In some embodiments, doses that could be used in the treatment of human subjects range from 1-10 mg/m$^2$, such as 1, 2, 3, 4, 5, 6, 7, 8, 9, or 10 mg/m$^2$. Effective doses can be extrapolated from dose-response curves derived from in vitro or animal model test systems.

A. Pharmaceutical Compositions

Also provided herein are pharmaceutical compositions and formulations comprising the DNA aptamer and a pharmaceutically acceptable carrier.

The pharmaceutical composition may comprise the present DNA aptamer in a pharmaceutically effective amount in the pharmaceutical composition. The medicament further comprises preferably suitable carrier material, excipients and the like. If necessary, the medicinal product may contain one or more other active ingredients. The active compounds can be also coupled to the DNA aptamer, i.e., covalently or non-covalently bound. Suitable formulations and dosage forms are known in the art or can be prepared in a routine manner according to the prior art. The aptamers of the invention can for example be bound to nanoparticles which are loaded with other active ingredients, whereby a targeted delivery of the active ingredients is made possible.

Pharmaceutical compositions and formulations as described herein can be prepared by mixing the active ingredients (such as a lipid or a polypeptide) having the desired degree of purity with one or more optional pharmaceutically acceptable carriers (Remington's Pharmaceutical Sciences 22$^{nd}$ edition, 2012), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol: and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn— protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.).

B. Combination Therapies

In certain embodiments, the compositions and methods of the present embodiments involve a DNA aptamer in combination with at least one additional therapy. The additional therapy may be radiation therapy, surgery (e.g., lumpectomy and a mastectomy), chemotherapy, gene therapy, DNA therapy, viral therapy, RNA therapy, immunotherapy, bone marrow transplantation, nanotherapy, monoclonal antibody therapy, or a combination of the foregoing. The additional therapy may be in the form of adjuvant or neoadjuvant therapy. In specific embodiments, the additional therapy is chemotherapy, specifically paclitaxel or cisplatin.

In some embodiments, the additional therapy is the administration of small molecule enzymatic inhibitor or anti-metastatic agent. In some embodiments, the additional therapy is the administration of side-effect limiting agents (e.g., agents intended to lessen the occurrence and/or severity of side effects of treatment, such as anti-nausea agents, etc.). In some embodiments, the additional therapy is radiation therapy. In some embodiments, the additional therapy is surgery. In some embodiments, the additional therapy is a combination of radiation therapy and surgery. In some embodiments, the additional therapy is gamma irradiation. In some embodiments, the additional therapy is therapy targeting PBK/AKT/mTOR pathway, HSP90 inhibitor, tubulin inhibitor, apoptosis inhibitor, and/or chemopreventative agent. The additional therapy may be one or more of the chemotherapeutic agents known in the art.

A DNA aptamer may be administered before, during, after, or in various combinations relative to an additional cancer therapy, such as immune checkpoint therapy. The administrations may be in intervals ranging from concurrently to minutes to days to weeks. In embodiments where the immune cell therapy is provided to a patient separately from an additional therapeutic agent, one would generally ensure that a significant period of time did not expire between the time of each delivery, such that the two compounds would still be able to exert an advantageously combined effect on the patient. In such instances, it is contemplated that one may provide a patient with the antibody therapy and the anti-cancer therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

Various combinations may be employed. For the example below a DNA aptamer is "A" and an anti-cancer therapy is "B":

A/B/A B/A/B B/B/A A/A/B A/B/B B/A/A A/B/B/B B/A/B/B

B/B/B/A B/B/A/B A/A/B/B A/B/A/B A/B/B/A B/B/A/A

B/A/B/A B/A/A/B A/A/A/B B/A/A/A A/B/A/A A/A/B/A

Administration of any compound or therapy of the present embodiments to a patient will follow general protocols for the administration of such compounds, taking into account the toxicity, if any, of the agents. Therefore, in some embodiments there is a step of monitoring toxicity that is attributable to combination therapy.

1. Chemotherapy

A wide variety of chemotherapeutic agents may be used in accordance with the present embodiments. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan): bryostatin; callystatin: CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TM1): eleutherobin: pancratistatin; a sarcodictyin; spongistatin; nitrogen mustards, such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, and uracil mustard: nitrosureas, such as carmustine, chlorozotocin, fotemustine, lomustine, nimustine, and ranimnustine: antibiotics, such as the enediyne antibiotics (e.g., calicheamicin, especially calicheamicin gammaI1 and calicheamicin omegaI1); dynemicin, including dynemicin A: bisphosphonates, such as clodronate; an esperamicin; as well as neocarzinostatin chromophore and related chromoprotein enediyne antibiotic chromophores, aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid: eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone: 2,2',2"-trichlorotriethylamine; trichothecenes (especially T-2 toxin, verracurin A, roridin A and anguidine): urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine: mercaptopurine: platinum coordination complexes, such as cisplatin, oxaliplatin, and carboplatin: vinblastine; platinum; etoposide (VP-16); ifosfamide; mitoxantrone; vincristine, vinorelbine; novantrone; teniposide; edatrexate; daunomycin; aminopterin; xeloda; ibandronate; irinotecan (e.g., CPT-11); topoisomerase inhibitor RFS 2000; difluoromethylornithine (DMFO); retinoids, such as retinoic acid; capecitabine; carboplatin, procarbazine, plicomycin, gemcitabien, navelbine, farnesyl-protein transferase inhibitors, transplatinum, and pharmaceutically acceptable salts, acids, or derivatives of any of the above.

2. Radiotherapy

Other factors that cause DNA damage and have been used extensively include what are commonly known as γ-rays. X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

3. Immunotherapy

The skilled artisan will understand that additional immunotherapies may be used in combination or in conjunction with methods of the embodiments. In the context of cancer treatment, immunotherapeutics, generally, rely on the use of immune effector cells and molecules to target and destroy cancer cells. Rituximab (RITUXAN®) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve as a targeting agent. Alternatively, the effector may be a lymphocyte carrying a surface molecule that interacts, either directly or indirectly, with a tumor cell target. Various effector cells include cytotoxic T cells and NK cells Antibody-drug conjugates (ADCs) comprise monoclonal antibodies (MAbs) that are covalently linked to cell-killing drugs. This approach combines the high specificity of MAbs against their antigen targets with highly potent cytotoxic drugs, resulting in "armed" MAbs that deliver the payload (drug) to tumor cells with enriched levels of the antigen. Targeted delivery of the drug also minimizes its exposure in normal tissues, resulting in decreased toxicity and improved therapeutic index. The approval of two ADC drugs, ADCETRIS® (brentuximab vedotin) in 2011 and KADCYLA® (trastuzumab emtansine or T-DM1) in 2013 by FDA validated the approach. There are currently more than 30 ADC drug candidates in various stages of clinical trials for cancer treatment. As antibody engineering and linker-payload optimization are becoming more and more mature, the discovery and development of new ADCs are increasingly dependent on the identification and validation of new targets that are suitable to this approach and the generation of targeting MAbs. Two criteria for ADC targets are upregulated/high levels of expression in tumor cells and robust internalization.

In one aspect of immunotherapy, the tumor cell must bear some marker that is amenable to targeting, i.e., is not present on the majority of other cells. Many tumor markers exist and any of these may be suitable for targeting in the context of the present embodiments. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies are immune adjuvants, e.g., *Mycobacterium bovis*, Plasmodium falciparum, dinitrochlorobenzene, and aromatic compounds; cytokine therapy, e.g., interferons α, β, and γ, IL-1. GM-CSF, and TNF; gene therapy, e.g., TNF. IL-1, IL-2, and p53; and monoclonal antibodies, e.g., anti-CD20, anti-ganglioside GM2, and anti-p185. It is contemplated that one or more anti-cancer therapies may be employed with the antibody therapies described herein.

In some embodiments, the immunotherapy may be an immune checkpoint inhibitor. Immune checkpoints either turn up a signal (e.g., co-stimulatory molecules) or turn down a signal. Inhibitory immune checkpoints that may be targeted by immune checkpoint blockade include adenosine A2A receptor (A2AR), B7-H3 (also known as CD276), B and T lymphocyte attenuator (BTLA), cytotoxic T-lymphocyte-associated protein 4 (CTLA-4, also known as CD152), indoleamine 2,3-dioxygenase (IDO), killer-cell immunoglobulin (KIR), lymphocyte activation gene-3 (LAG3), programmed death 1 (PD-1), T-cell immunoglobulin domain and mucin domain 3 (TIM-3) and V-domain Ig suppressor of T cell activation (VISTA). In particular, the immune checkpoint inhibitors target the PD-1 axis and/or CTLA-4.

The immune checkpoint inhibitors may be drugs such as small molecules, recombinant forms of ligand or receptors, or, in particular, are antibodies, such as human antibodies (e.g., International Patent Publication WO2015016718; Pardoll, *Nat Rev Cancer*. 12(4): 252-64, 2012; both incorporated herein by reference). Known inhibitors of the immune checkpoint proteins or analogs thereof may be used, in particular chimerized, humanized or human forms of antibodies may be used. As the skilled person will know, alternative and/or equivalent names may be in use for certain antibodies mentioned in the present disclosure. Such alternative and/or equivalent names are interchangeable in the context of the present disclosure. For example it is known that lambrolizumab is also known under the alternative and equivalent names MK-3475 and pembrolizumab.

In some embodiments, the PD-1 binding antagonist is a molecule that inhibits the binding of PD-1 to its ligand binding partners. In a specific aspect, the PD-1 ligand binding partners are PDL1 and/or PDL2. In another embodiment, a PDL1 binding antagonist is a molecule that inhibits the binding of PDL1 to its binding partners. In a specific aspect, PDL1 binding partners are PD-1 and/or B7-1. In another embodiment, the PDL2 binding antagonist is a molecule that inhibits the binding of PDL2 to its binding partners. In a specific aspect, a PDL2 binding partner is PD-1. The antagonist may be an antibody, an antigen binding fragment thereof, an immunoadhesin, a fusion protein, or oligopeptide. Exemplary antibodies are described in U.S. Pat. Nos. 8,735,553, 8,354,509, and 8,008,449, all incorporated herein by reference. Other PD-1 axis antagonists for use in the methods provided herein are known in the art such as described in U.S. Patent Application No. US20140294898, US2014022021, and US20110008369, all incorporated herein by reference.

In some embodiments, the PD-1 binding antagonist is an anti-PD-1 antibody (e.g., a human antibody, a humanized antibody, or a chimeric antibody). In some embodiments, the anti-PD-1 antibody is selected from the group consisting of nivolumab, pembrolizumab, and CT-011. In some embodiments, the PD-1 binding antagonist is an immunoadhesin (e.g., an immunoadhesin comprising an extracellular or PD-1 binding portion of PDL1 or PDL2 fused to a constant region (e.g., an Fc region of an immunoglobulin sequence). In some embodiments, the PD-1 binding antagonist is AMP-224. Nivolumab, also known as MDX-1106-04, MDX-1106, ONO-4538, BMS-936558, and OPDIVO®, is an anti-PD-1 antibody described in WO2006/121168. Pembrolizumab, also known as MK-3475. Merck 3475, lambrolizumab, KEYTRUDA®, and SCH-900475, is an anti-PD-1 antibody described in WO2009/114335. CT-011, also known as hBAT or hBAT-1, is an anti-PD-1 antibody described in WO2009/101611. AMP-224, also known as B7-DCIg, is a PDL2-Fc fusion soluble receptor described in WO2010/027827 and WO2011/066342.

Another immune checkpoint that can be targeted in the methods provided herein is the cytotoxic T-lymphocyte-associated protein 4 (CTLA-4), also known as CD152. The complete cDNA sequence of human CTLA-4 has the Genbank accession number L15006. CTLA-4 is found on the surface of T cells and acts as an "off" switch when bound to CD80 or CD86 on the surface of antigen-presenting cells. CTLA4 is a member of the immunoglobulin superfamily that is expressed on the surface of Helper T cells and transmits an inhibitory signal to T cells. CTLA4 is similar to the T-cell co-stimulatory protein, CD28, and both molecules bind to CD80 and CD86, also called B7-1 and B7-2 respectively, on antigen-presenting cells. CTLA4 transmits an inhibitory signal to T cells, whereas CD28 transmits a stimulatory signal. Intracellular CTLA4 is also found in regulatory T cells and may be important to their function. T cell activation through the T cell receptor and CD28 leads to increased expression of CTLA-4, an inhibitory receptor for B7 molecules.

In some embodiments, the immune checkpoint inhibitor is an anti-CTLA-4 antibody (e.g., a human antibody, a humanized antibody, or a chimeric antibody), an antigen binding fragment thereof, an immunoadhesin, a fusion protein, or oligopeptide.

Anti-human-CTLA-4 antibodies (or VH and/or VL domains derived therefrom) suitable for use in the present methods can be generated using methods well known in the art. Alternatively, art recognized anti-CTLA-4 antibodies can be used. For example, the anti-CTLA-4 antibodies disclosed in: U.S. Pat. No. 8,119,129, WO 01/14424, WO 98/42752; WO 00/37504 (CP675,206, also known as tremelimumab; formerly ticilimumab), U.S. Pat. No. 6,207,156; Hurwitz et al. (1998) *Proc Natl Acad Sci USA* 95(17): 10067-10071; Camacho et al. (2004) *J Clin Oncology* 22(145): Abstract No. 2505 (antibody CP-675206); and Mokyr et al. (1998) *Cancer Res* 58:5301-5304 can be used in the methods disclosed herein. The teachings of each of the aforementioned publications are hereby incorporated by reference. Antibodies that compete with any of these art-recognized antibodies for binding to CTLA-4 also can be used. For example, a humanized CTLA-4 antibody is described in International Patent Application No. WO2001014424, WO2000037504, and U.S. Pat. No. 8,017, 114; all incorporated herein by reference.

An exemplary anti-CTLA-4 antibody is ipilimumab (also known as 10D1, MDX-010, MDX-101, and Yervoy®) or antigen binding fragments and variants thereof (see, e.g., WO 01/14424). In other embodiments, the antibody comprises the heavy and light chain CDRs or VRs of ipilimumab. Accordingly, in one embodiment, the antibody comprises the CDR1, CDR2, and CDR3 domains of the VH region of ipilimumab, and the CDR1, CDR2 and CDR3 domains of the VL region of ipilimumab. In another embodiment, the antibody competes for binding with and/or binds to the same epitope on CTLA-4 as the above-mentioned antibodies. In another embodiment, the antibody has at least about 90% variable region amino acid sequence identity with the above-mentioned antibodies (e.g., at least about 90%, 95%, or 99% variable region identity with ipilimumab).

Other molecules for modulating CTLA-4 include CTLA-4 ligands and receptors such as described in U.S. Pat. Nos. 5,844,905, 5,885,796 and International Patent Application Nos. WO1995001994 and WO1998042752; all incorporated herein by reference, and immunoadhesins such as described in U.S. Pat. No. 8,329,867, incorporated herein by reference.

4. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

5. Other Agents

It is contemplated that other agents may be used in combination with certain aspects of the present embodiments to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy.

IV. ARTICLES OF MANUFACTURE OR KITS

An article of manufacture or a kit is provided comprising DNA aptamers is also provided herein. The article of manufacture or kit can further comprise a package insert comprising instructions for using the DNA aptamers to treat or delay progression of cancer in an individual or to enhance immune function of an individual having cancer. Any of the antigen-specific DNA aptamers described herein may be included in the article of manufacture or kits. Suitable containers include, for example, bottles, vials, bags and syringes. The container may be formed from a variety of materials such as glass, plastic (such as polyvinyl chloride or polyolefin), or metal alloy (such as stainless steel or hastelloy). In some embodiments, the container holds the formulation and the label on, or associated with, the container may indicate directions for use. The article of manufacture or kit may further include other materials desirable from a commercial and user standpoint, including other buffers, diluents, filters, needles, syringes, and package inserts with instructions for use. In some embodiments, the article of manufacture further includes one or more of another agent (e.g., a chemotherapeutic agent, and anti-neoplastic agent). Suitable containers for the one or more agent include, for example, bottles, vials, bags and syringes.

V. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—DNA Aptamer Development and Characterization

Figure 6B:
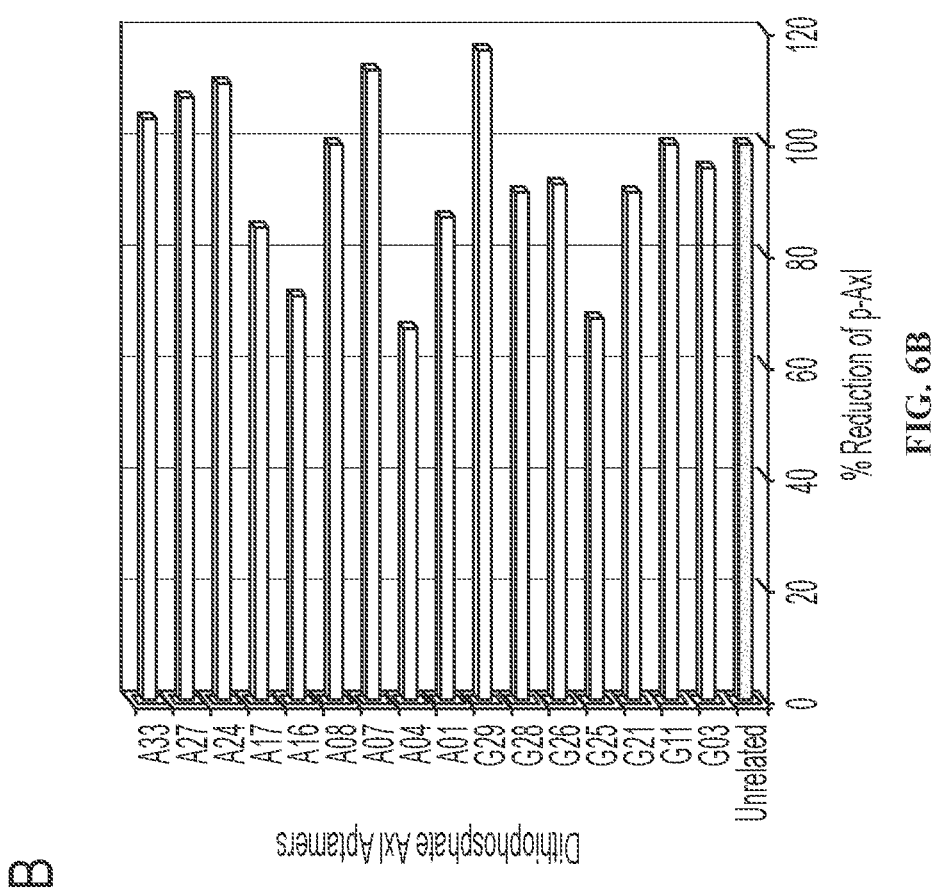

In this study, two aptamers GLB-G25 and GLB-A04 were characterized based on their ability to reduce p-AXL expression (FIG. 6B) in ovarian cancer cell line, from a library of seventeen different DNA aptamers that differ from each other with respect to the position and the nucleic acid base of the dithiophosphate modification (FIG. 6A). The antitumor effects of GLB-G25 and GLB-A04 dithiophosphate and PEG modified aptamers were evaluated.

Figure 6C:
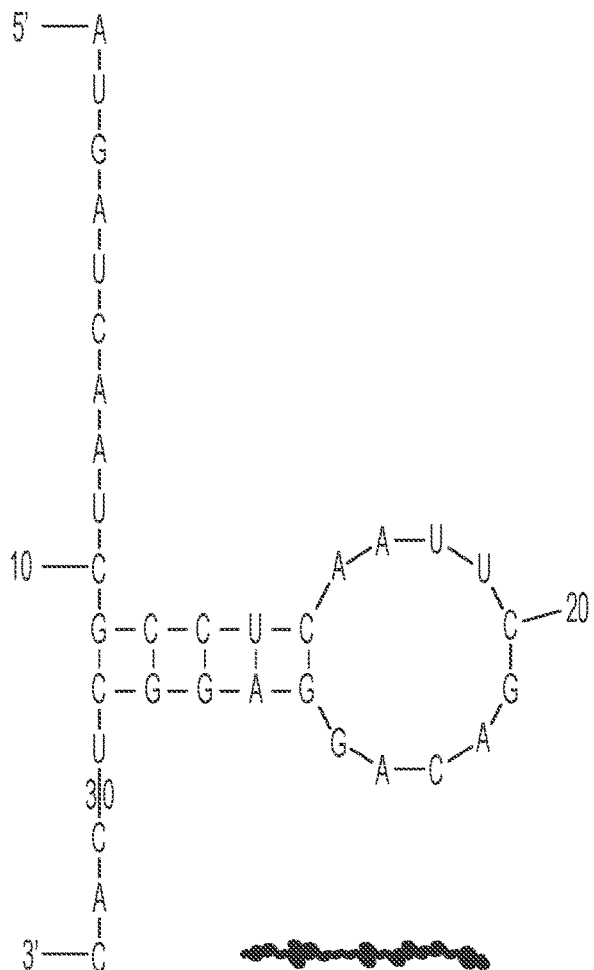
Figure 6C:
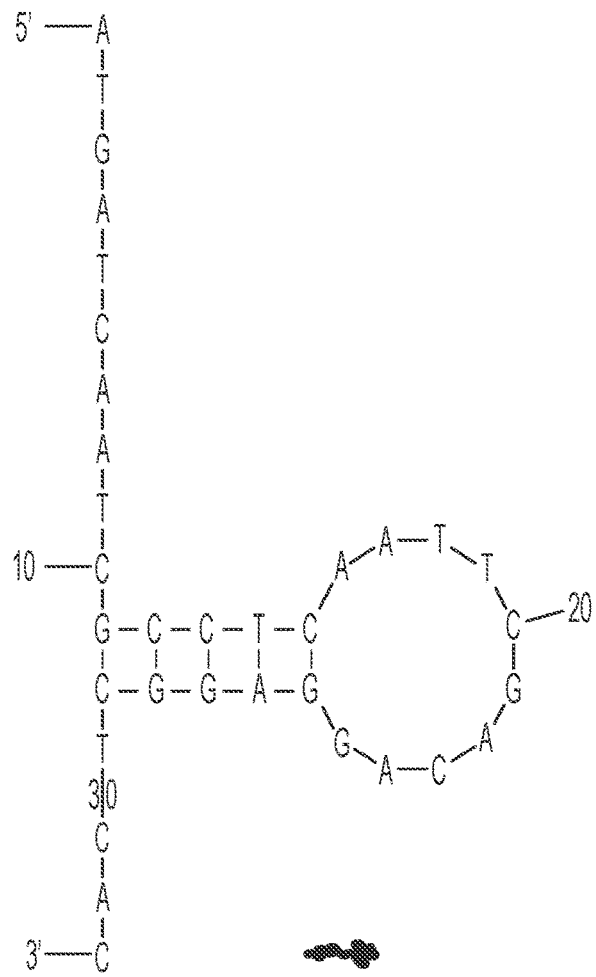

It was first determined if the addition of dithiophosphate groups could affect the three-dimensional structure of the aptamers by comparing the 2D and 3D structure of GL21.T with GLD-1, GLB-G25 and GLB-A04. The most stable predicted secondary structure, (predicted by MFold server (Zuker, 2003)), of RNA and DNA aptamers suggests that these aptamers fold in to hairpin like structures that consists 4 of regions: one head/loop region, one stem region and two single stranded ends (FIG. 6C). 3D models of RNA and DNA Aptamers were generated that satisfied secondary structure predictions by MFold server (FIG. 1).

In FIG. 1A, the position of 2'-fluoro pyrimidine (2'-F Py) modification, along the sequence, is represented by green dots for GL21.T, GLD-1, GLB-G25 and GLB-A04 aptamers, while the monothiophosphate (rectangles) and dithiophosphate groups (dots), show that the addition of the thiophosphate group does not alter the three-dimensional shape of the GLB-G25 and GLB-A04 aptamers compared with the previous two aptamers. The additional modifications, specifically on GLB-G25 lead to the formation of additional hydrogen bonds which could explain the higher binding and stability which leads to the observed higher in vivo inhibition of the AXL by GLB-G25.

Figure 2A:
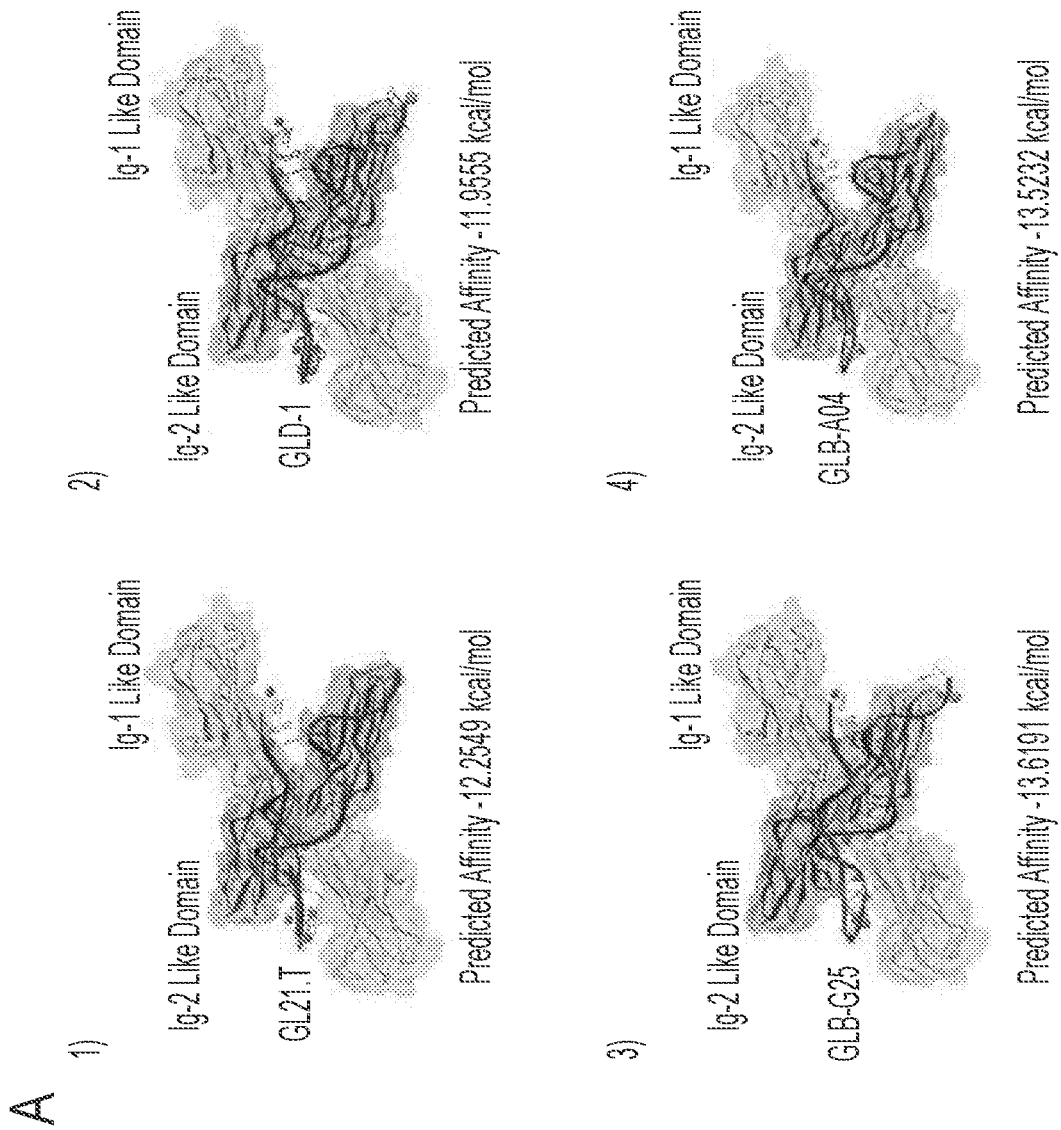
FIGS. 2A-2B: GL21.T, GLD-1, GLB-G25 and GLB-A04 bind extracellular domain of AXL in the centroid position; GLB-G25 and GLB-A04 strongly interact with AXL receptor. (A) Docking analysis 3D models of GL21.T, GLD-1, GLB-G25, and GLB-A04 aptamers in homology model of extracellular domain (ECD) of AXL receptor (dimer) (B) GLB-G25 and GLB-A04 have stronger interaction with AXL receptor compared with GL21.T and GLD-1 due to the additional hydrogen bonds formed (Table 1) and increased affinity (as shown by the lowered free energy) with the AXL receptor by the Aptamers.
Figure 2B:
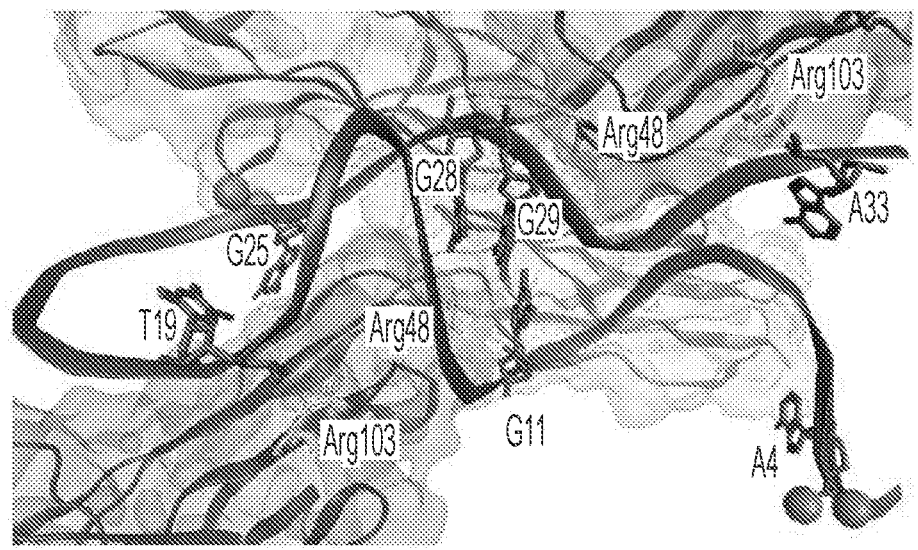

Next, the 3D models of GL21.T, GLD-1, GLB-G25, and GLB-A04 aptamers were docked in a homology model of the extracellular domain (ECD) of AXL receptor (dimer) using Autodock Vina software. The docking experiments generated consistent models that showed the interaction of the head and stem region of the aptamers with the centroid of the AXL model where dimerization occurs (FIG. 2A). The list of interacting residues between the GL21.T, GLD-1, GLB-G25, GLBA04 and AXL receptor are reported in Table 1. GLB-G25 (green) and GLBA04 (orange) strongly interact with Ig-like domain of AXL receptor compared with GL21.T and GLD-1 aptamers. Adenine 33 and thymine 19, interacting with arginine 103, are key bases that lead to the strong affinity of GLB-G25 and GLB-A04 with the AXL receptor (FIG. 2B).

Table 1: List of interacting residues (ionic pairs and hydrogen bonds) between the different GL21.T, GLD-1, GLB-25, and GLB-A04 and AXL receptor. GLB-G25 and GLB-A04 aptamers present the stronger interactions with Ig-like domain of AXL receptor compared with GL21.T and GLD-1 aptamers, supporting the idea that dithiophosphate modifications enhance the binding affinity.

| Sequence Name | Free Energy Scoring (kcal/mol) | Distance (Angstrom) | AXL interacting residues | Aptamer interacting residues |
| --- | --- | --- | --- | --- |
| GL21.T | −14.939 | 3.076 | Arg48 | G11 |
|  | −28.728 | 2.937 | Arg48 | G28 |
|  | −15.743 | 3.097 | Arg48 | G29 |
|  | −35.167 | 2.932 | Arg103 | A33 |
| GLD-1 | −14.16 | 3.397 | Arg48 | G28 |
|  | −11.171 | 3.328 | Arg48 | G29 |
|  | −32.933 | 3.06 | Arg103 | A33 |
| GLB-G25 | −15.074 | 3.374 | Arg48 | G28 |
|  | −12.959 | 3.237 | Arg48 | G29 |
|  | −19.778 | 3.084 | Arg103 | T19 |
|  | −38.128 | 3.063 | Arg103 | A33 |
| GLB-A04 | −15.082 | 3.373 | Arg48 | G28 |
|  | −12.959 | 3.238 | Arg48 | G29 |
|  | −16.99 | 3.168 | Arg103 | T19 |
|  | −38.127 | 3.063 | Arg103 | A33 |

Figure 3A:
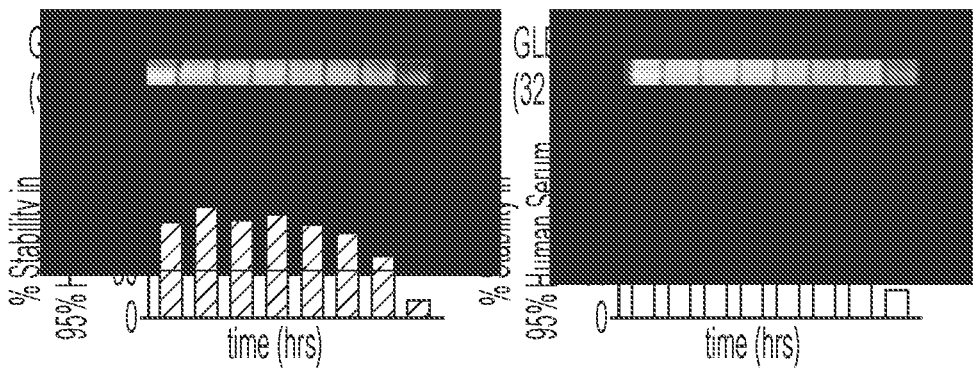

To determine stability, pharmacokinetics (PK) and biodistribution of GLB-G25 and GLBA04, 32 pmol of each aptamer were incubated in 95% human serum at 37° C. from 1 hour to 7 days and it was found that GLB-G25 and GLB-A04 were stable for up 72 hours (FIG. 3A) as shown by denaturing PAGE analysis. Since aptamer modifications and conjugations may have an effect on circulation, tissue accumulation, metabolism and clearance, the pharmacokinetic profiles of GLB-G25 and GLB-A04 were evaluated with and without PEG modification in vivo. The pharmacokinetic data showed that adding PEG increased the size of the aptamers, reduced time of elimination and clearance and increased the time and volume distribution (FIGS. 3B and C).

Figure 3D:
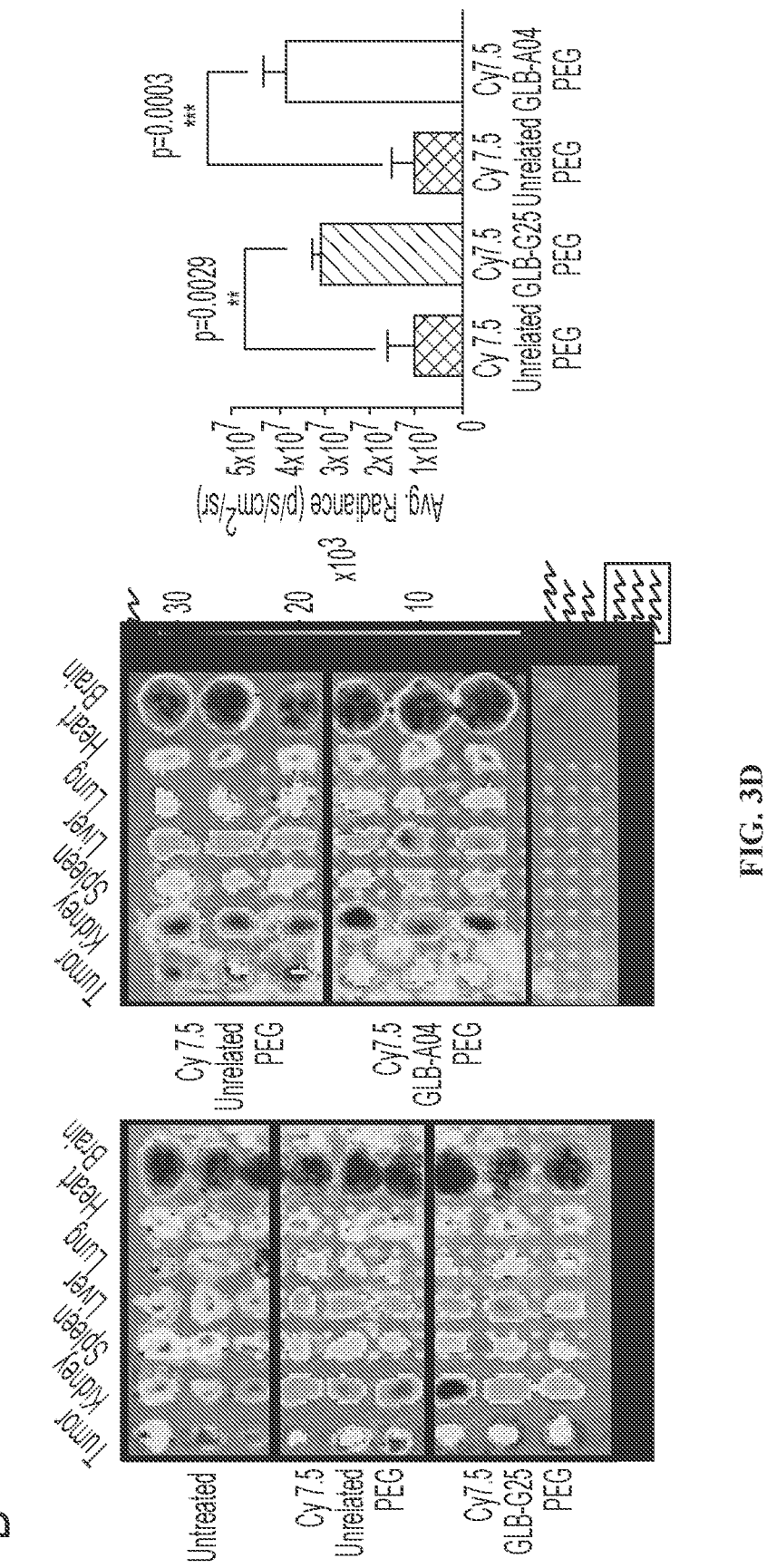

Mice bearing SKOV3.ip ovarian cancer cell lines were injected intravenously (via tail vein) with Cy7.5 labeled GLB-G25 and Cy7.5 labeled GLB-A04 and imaged 2 hours post injection. The ex vivo biodistribution data showed that GLB-G25 and GLB-A04 significantly target tumors compared with unrelated aptamer. The GLB-G25 and GLB-A04 uptake in kidney, spleen, liver and lung was high, lower in the heart, and no uptake was shown in brain (FIG. 3D).

Figure 4A:
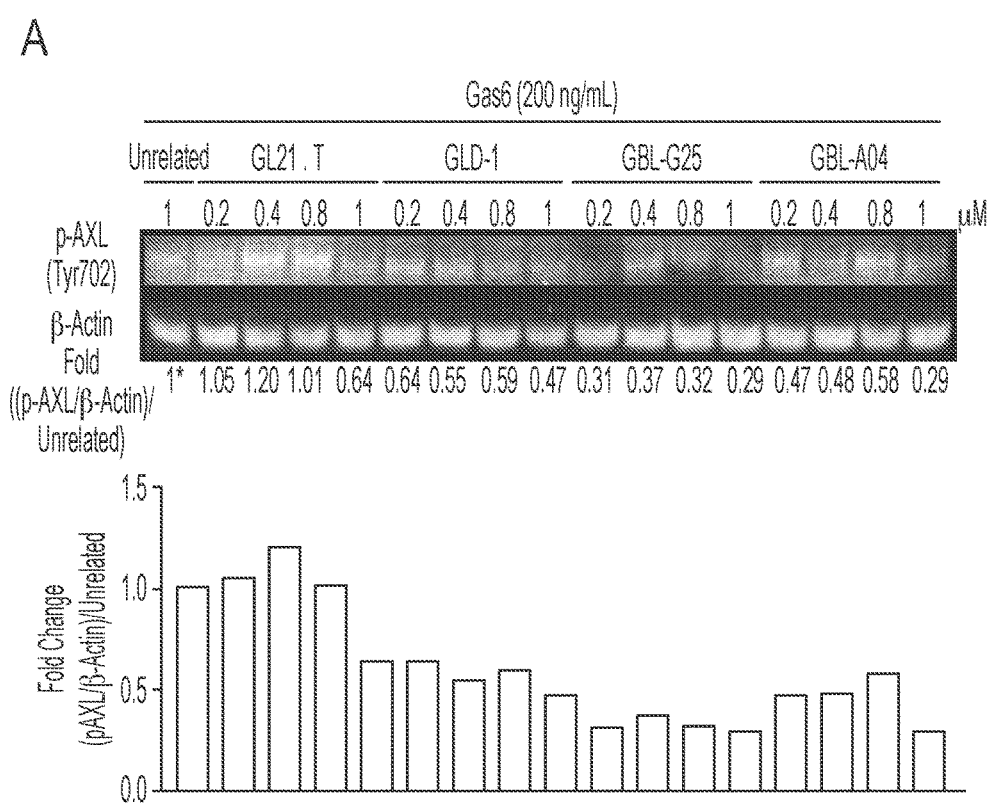
FIGS. 4A-4C: GLB-G25 and GLB-A04 reduce p-AXL expression, invasion and migration in OC cell line. (A) GLB-G25 and GLB-A04 strongly reduce p-AXL expression following the treatment with Gas 6 ligand at all the concentrations compared with GL21.T and GLD-1 aptamers in SKOV3.ip1 cell line (B) Cell invasion in SKOV3.ip1 and OVCAR5 cell lines. (C) Wound healing in SKOV3.ip1 and OVCAR5 cell line.

In order to determine whether the GLB-G25 and GLB-A04 had a better effect on the activity of AXL following Gas 6 stimulation, the SKOV3.ip ovarian cancer cell line (AXL is highly expressed in some of the ovarian cancer cell (OC) lines analyzed, especially in SKOV3.ip and OVCAR5 cell line (FIG. 4A)) was treated with RNA and DNA aptamers at different concentrations. The data showed that GLB-G25 and GLB-A04 have a better ability to reduce the expression of p-AXL, showing that the dithiophosphate modifications improved the activity of the aptamers compared to monothio modifications.

Figures 4B, 4C:
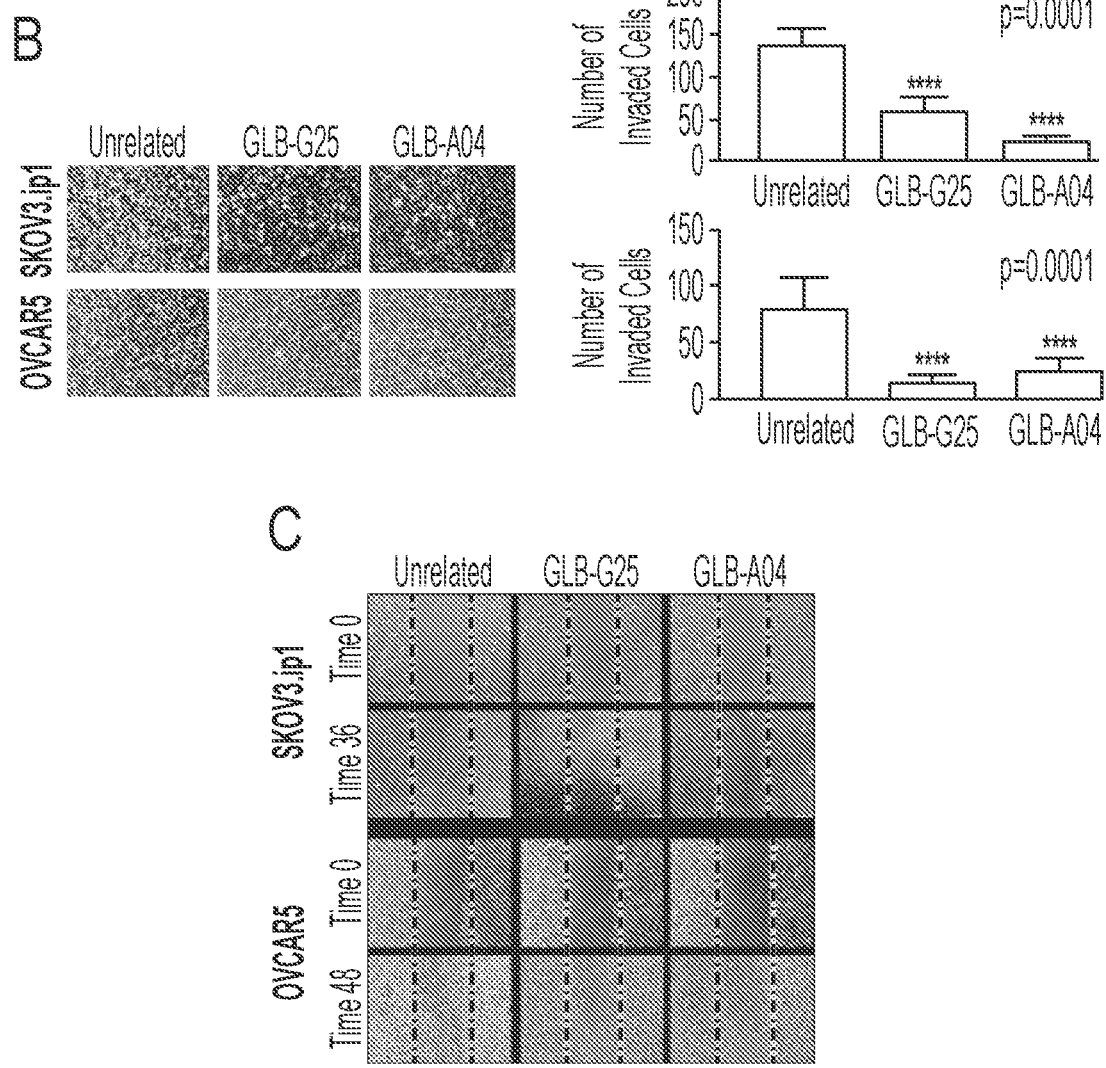

Immunoblotting analysis showed that GLB-G25 and GLB-A04 (400 nM) significantly reduced p-AXL expression in SKOV3.ip and OVCAR5 cell lines following Gas 6 stimulation (FIG. 4B). To elucidate the effects of GLB-G25 and GLB-A04 on cancer metastasis, invasion and migration were analyzed in SKOV3-ip1 and OVCAR5 cells treated with GLB-G25 and GLB-A04 (400 nM). The treatment with GLB-G25 and GLB-A04 significantly reduced invasion (FIG. 4C) and migration (FIG. 4D) in both cell lines.

Figures 5A, 5B, 5C, 5D:
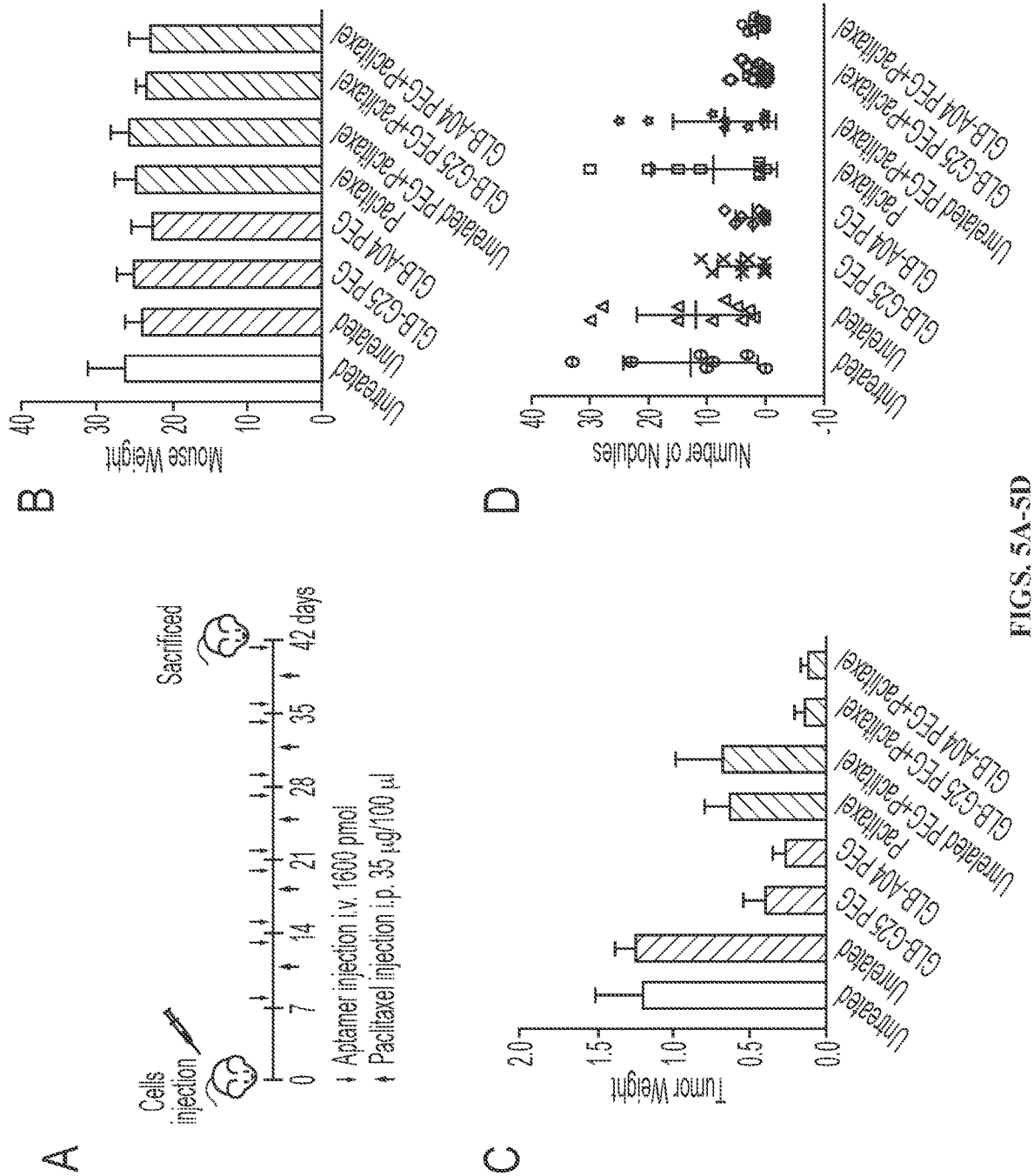
FIGS. 5A-5F: Determination of antitumor activity of GLB-G25 and GLB-A04 in vivo. (A) Scheme of treatment for orthotopic animal models. (B) Mouse weight in mice bearing OVCR 5 ovarian cancer cell line. (C) Tumor weight in mice bearing OVCR 5 ovarian cancer cell line. (D) Number of tumor nodules in mice bearing OVCR 5 ovarian cancer cell line. (E-F) Immunoblotting analysis for p-AXL expression in tumor tissues from mice bearing SKOV3.ip1 ovarian cancer cell line.
Figures 5E, 5F:
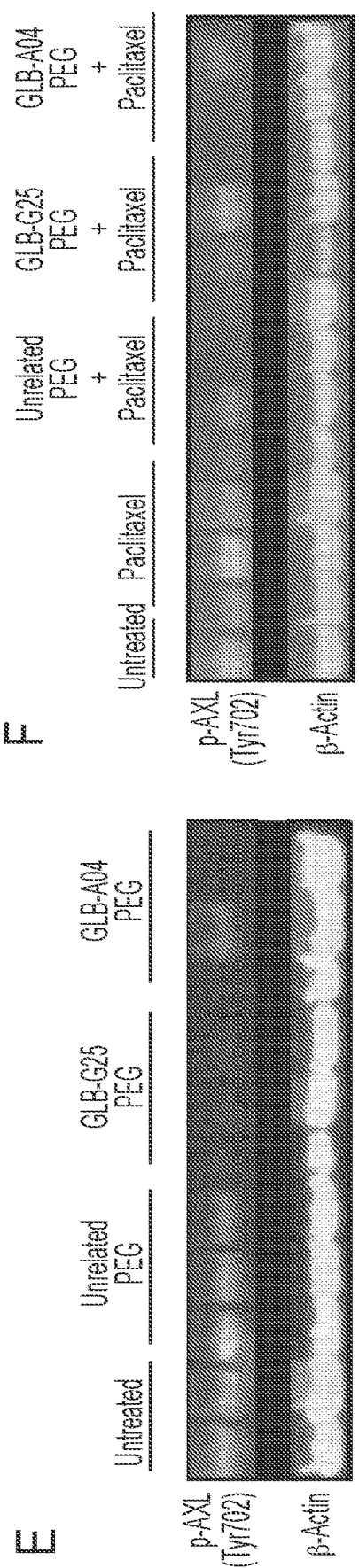

The antitumor activity was assessed in two orthotopic SKOV3.ip1 and OVAR5 animal models (n=10 for each group in both animal model). Ovarian cancer cell lines were injected intraperitoneally. GLB-G25 PEG and GLB-A04 PEG were injected intravenously twice a week alone or in combination with paclitaxel injected intraperitoneally once a week (FIG. 5A). A significant therapeutic effect was observed in both in vivo models. GLB-G25 PEG and GLB-A04 PEG alone or in combination with paclitaxel significantly reduced tumor weight and the number of tumor nodules (FIGS. 5C and D), without any effect on the body weight of the mice, indicating that the GLB-G25 PEG and GLB-A04 PEG, treatments were not toxic (FIG. 5B).

Figures 7A, 7B, 7C, 7D:
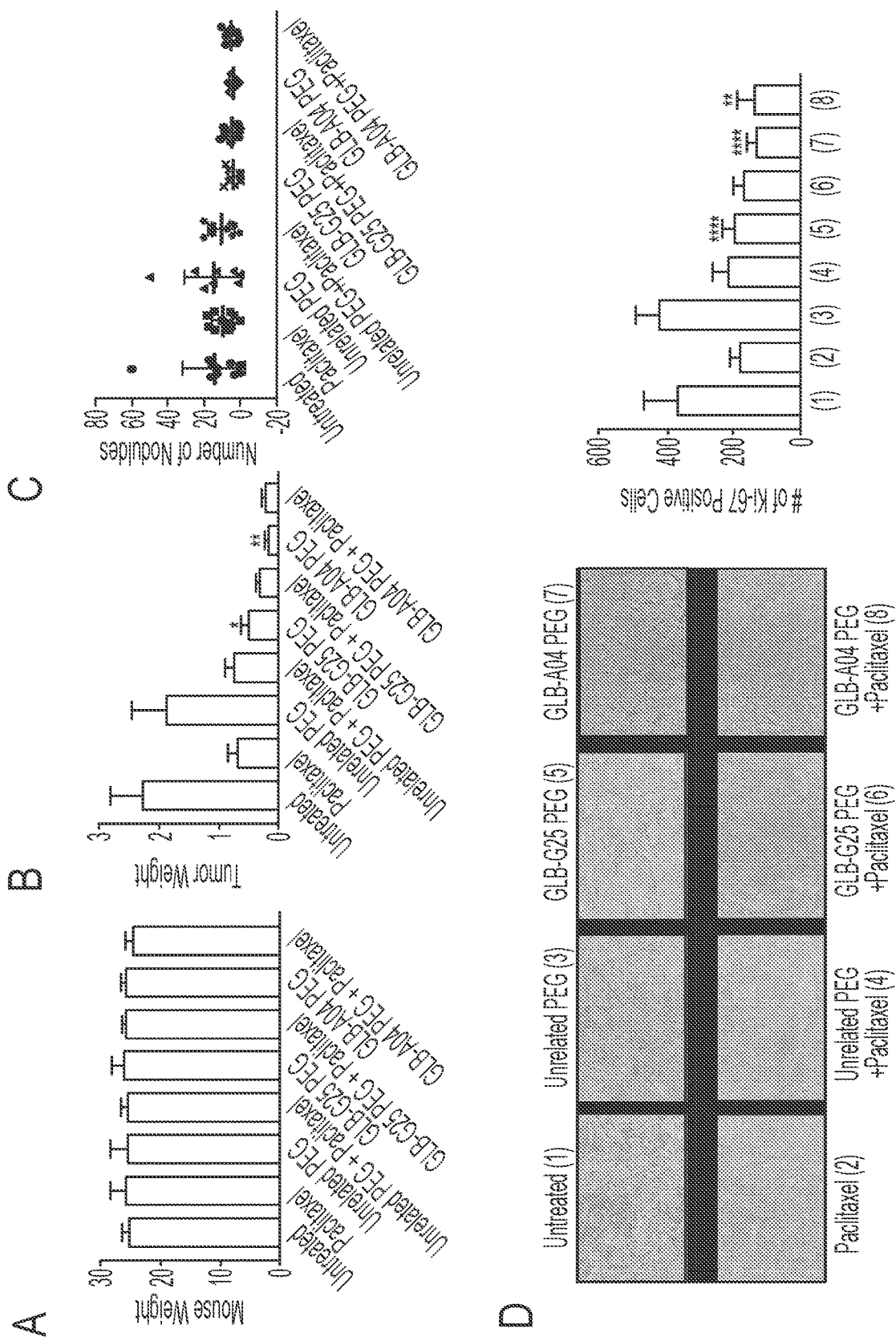
FIGS. 7A-7E: Effect of candidates on orthotopic animal models in SKOV3.ip1. (A) Mouse weight in SKOV3.ip1 animal model. (B) Tumor weight in SKOV3 animal model. (C) Number of tumor nodules in SKOV3.ip1 animal model. (D-E) Immunohistochemistry analysis for K167 and CD31 in SKOV3.ip1 animal model.
Figure 7E:
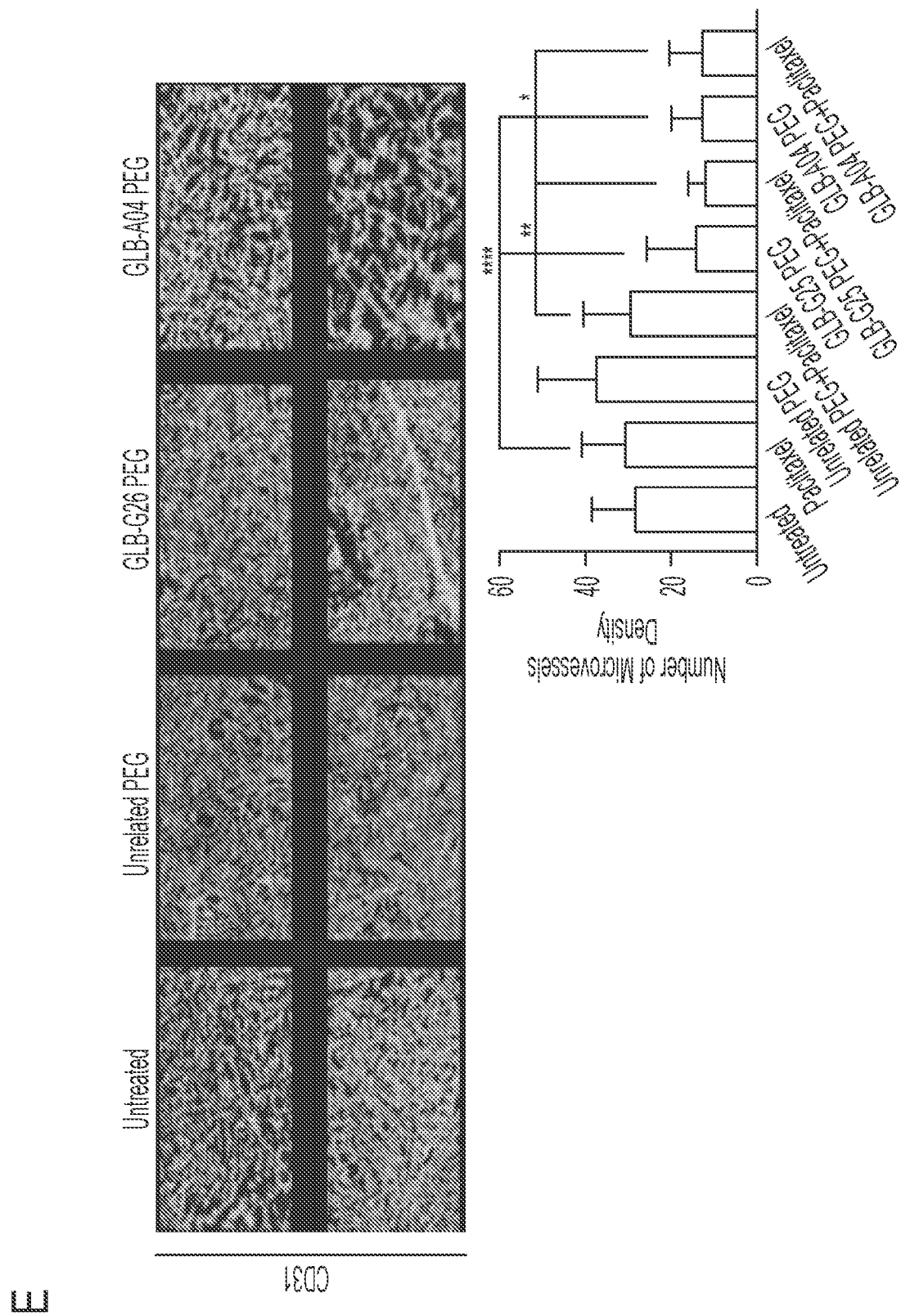

Immunohistochemical analysis of tumor tissues revealed that the SKOV3-IP1 tumor-bearing mice treated with GLB-G25 PEG and GLB-A04 PEG alone or in combination with paclitaxel significantly reduced cell proliferation (FIG. 7D).

Next, it was assessed whether GLB-25 PEG and GLB-A04 PEG could reduce p-AXL expression in tumor tissue from mice bearing SKOV3.ip1 ovarian cancer cell line. It was demonstrated that GLB-G25 PEG and GLB-A04 PEG alone or in combination with paclitaxel significantly reduced p-AXL expression. Taken together the data demonstrate that the present design of the aptamer with dithiophosphate and PEG modifications improved the in vivo anti-tumor activity against AXL.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Camacho et al., *J Clin Oncology* 22(145): Abstract No. 2505, 2004.
Hurwitz et al., *Proc Natl Acad Sci USA* 95(17): 10067-10071, 1998.
International Patent Publication No. WO2001014424
International Patent Publication No. WO2000037504
International Patent Publication No. WO2006/121168
International Patent Publication No. WO2009/101611
International Patent Publication No. WO2009/114335
International Patent Publication No. WO2010/027827
International Patent Publication No. WO2011/066342
International Patent Publication No. WO2015016718
Mokyr et al., *Cancer Res* 58:5301-5304, 1998.
Pardoll, *Nat Rev Cancer*, 12(4): 252-64, 2012.
U.S. Pat. No. 4,870,287
U.S. Pat. No. 5,760,395
U.S. Pat. No. 5,844,905
U.S. Pat. No. 5,885,796
U.S. Pat. No. 8,008,449
U.S. Pat. No. 8,017,114
U.S. Pat. No. 8,119,129
U.S. Pat. No. 8,329,867
U.S. Pat. No. 8,354,509
U.S. Pat. No. 8,735,553
International Patent Application No. WO1995001994
International Patent Application No. WO1998042752
U.S. Patent Publication No. US20110008369
U.S. Patent Publication No. US20140022021
U.S. Patent Publication No. US20140294898
Zuker M. Mfold web server for nucleic acid folding and hybridization prediction. *Nucleic Acids Res*, 31(13): 3406-3415, 2003.

What is claimed is:

1. An AXL receptor-kinase binding DNA aptamer comprising a dithiophosphate backbone linkage, wherein the sequence of the DNA aptamer is at least 95% identical to the sequence of SEQ ID NO: 1, and wherein the dithiophosphate backbone is (i) at position 25 of SEQ ID NO: 1 or (ii) at position 4 of SEQ ID NO: 1.

2. The aptamer of claim 1, wherein the sequence of the DNA aptamer is the sequence of SEQ ID NO:1.

3. The aptamer of claim 1, wherein the aptamer has a length of 34 nucleotides.

4. The aptamer of claim 1, wherein all of the pyrimidines are chemically modified with 2'-fluoropyrimidine.

5. The aptamer of claim 1, wherein the aptamer is polyethylene glycol (PEG) modified.

6. The aptamer of claim 5, wherein the PEG is conjugated to the 5' end of the aptamer.

7. The aptamer of claim 6, wherein the PEG is maleimide PEG.

8. The aptamer of claim 1, wherein the aptamer is single-stranded.

9. The aptamer of claim 8, wherein the aptamer folds into a hairpin-like structure comprising a loop region, a stem region, and two single-stranded ends.

10. The aptamer of claim 1, wherein the aptamer further comprises a detectable label.

11. A pharmaceutical composition comprising a DNA aptamer of claim 1 and a pharmaceutically acceptable carrier.

12. A method of treating a disease or disorder in a subject comprising administering an effective amount of a DNA aptamer of claim 1 to the subject.

13. A method for the detection of AXL receptor kinase comprising:
   (a) incubating a sample with a DNA aptamer of claim 1; and
   (b) measuring the binding of the DNA aptamer to the sample.

14. The aptamer of claim 1, wherein the aptamer further comprises one or more monothiophosphate backbone linkage.

* * * * *